United States Patent [19]

Helgstrand et al.

[11] 4,372,894
[45] Feb. 8, 1983

[54] PHOSPHONOFORMIC ACID ESTERS

[75] Inventors: Åke J. E. Helgstrand; Karl N. Johannson, both of Enhörna; Alfons Misiorny, Bandhagen; Jan O. Norén, Grödinge; Göran Stening, Soödertälje, all of Sweden

[73] Assignee: Astra Läkemedel Aktiebolag, Södertälje, Sweden

[21] Appl. No.: 93,166

[22] Filed: Nov. 13, 1979

Related U.S. Application Data

[63] Continuation-in-part of Ser. No. 971,689, Dec. 2, 1979, abandoned.

[30] Foreign Application Priority Data

| Dec. 22, 1977 [GB] | United Kingdom | 53580/77 |
| Dec. 22, 1977 [GB] | United Kingdom | 53581/77 |
| Dec. 22, 1977 [GB] | United Kingdom | 53582/77 |
| Dec. 22, 1977 [GB] | United Kingdom | 53583/77 |
| Jul. 3, 1978 [GB] | United Kingdom | 28548/78 |
| Jul. 3, 1978 [GB] | United Kingdom | 28552/78 |
| Jul. 3, 1978 [GB] | United Kingdom | 28553/78 |
| Jul. 3, 1978 [GB] | United Kingdom | 28555/78 |

[51] Int. Cl.³ .................... C07F 9/40; A61K 31/66
[52] U.S. Cl. .................... 260/941; 260/924; 544/110; 424/210; 424/199
[58] Field of Search .................... 260/941

[56] References Cited

U.S. PATENT DOCUMENTS

| 3,155,597 | 11/1964 | Cornell et al. | 202/39.5 |
| 3,533,995 | 10/1970 | Stewart et al. | 260/45.85 |
| 3,846,512 | 11/1974 | Langsdorf | 260/943 |
| 3,849,102 | 11/1974 | Bucha et al. | 71/76 |
| 3,943,201 | 3/1976 | McIntosh | 260/941 |
| 3,997,544 | 12/1976 | Langsdorf | 71/81 |
| 4,052,439 | 10/1977 | Herrin et al. | 560/129 |

FOREIGN PATENT DOCUMENTS

| 3275 | 8/1979 | European Pat. Off. |
| 2435407 | 8/1975 | Fed. Rep. of Germany |
| 77666 | 6/1977 | Luxembourg |
| 1243857 | 8/1971 | United Kingdom |
| 1317768 | 5/1973 | United Kingdom |

OTHER PUBLICATIONS

Shahak, C.A. vol. 65 (1966) 3785b.
Shahak et al. C.A. vol. 66 (1967) 55552z.
Shotani et al. C.A. vol. 79 (1973) 104712f.
Derwent 53335A/29 4/14/77.
Arburn et al. Pan. L. L. (1927) pp. 291-295.
Shahak et al. Israel J. of Chem., vol. 4 (1966) 225-231.
Shiotani et al. Ch. Pharm. Bull., vol. 21 (1973) pp. 1160-1163.
Nylan, Berichte, vol. 57B (1924) p. 1036.
Arbuzov et al., C.A. vol. 8 (1964) p. 2551.
Arbuzov et al., C.A. vol. 21 (1927) p. 1627.
Abruzov et al., C.A. vol. 42 (1948) pp. 4523g-4532.
Kamai et al., C.A. vol. 45 (1951) p. 542f.
Kamai et al., C.A. vol. 50 (1956), 794d.
Tahamizawa et al., C.A. vol. 61 (1964) 3104f-3105a.
Cornell et al., C.A. vol. 62 (1965) 1498c.
Tahamizawa et al., C.A. vol. 62 (1965) 16656.

*Primary Examiner*—Anton H. Sutto
*Attorney, Agent, or Firm*—Brumbaugh, Graves, Donohue & Raymond

[57] ABSTRACT

A compound of the formula

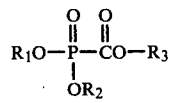

wherein $R_1$, $R_2$ and $R_3$ are the same or different, and each is selected from the group consisting of hydrogen and phenyl groups of the formula

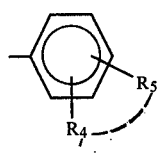

wherein $R_4$ and $R_5$ are the same or different and each is selected from the group consisting of hydrogen, halogen, alkyl having 1, 2, or 3 carbon atoms, alkoxy having 1, 2, or 3 carbon atoms, alkoxycarbonyl having 2-7 carbon atoms; and alkylcarbonyl groups having 2-7 carbon atoms; or $R_4$ and $R_5$ together from a straight saturated alkylene chain having 3 or 4 carbon atoms and being bound to adjacent positions, i.e. 2,3- or 3,4- in the phenyl ring; provided that one of $R_1$ and $R_2$ is a phenyl group of the formula II when $R_3$ is H; and physiologically acceptable salts and optical isomers thereof; methods for preparation of the compounds, pharmaceutical compositions containing them, and their medicinal use.

18 Claims, No Drawings

PHOSPHONOFORMIC ACID ESTERS

This application is a continuation in part application of the abandoned application Ser. No. 971,689 filed Dec. 2, 1978.

FIELD OF THE INVENTION

The present invention relates to novel compounds, methods for their preparation, novel pharmaceutical compositions and to a novel method for selectively combatting viruses, such as herpes viruses, influenza viruses, RNA tumor viruses, etc., which can cause various diseases in animals including man. Such diseases include both common infections and neoplastic disease, i.e. cancer.

BACKGROUND OF THE INVENTION

The effects of viruses on bodily functions is the end result of changes occuring at the cellular and subcellular levels. The pathogenic changes at the cellular level are different for different combinations of viruses and host cells. While some viruses cause a general destruction (killing) of certain cells, other may transform cells to a neoplastic state.

Important common viral infections are herpes dermatitis (including herpes labialis), herpes keratitis, herpes genitalis, herpes zoster, herpes encephalitis, infectious mononucleosis and cytomegalovirus infections all of which are caused by viruses belonging to the herpesvirus group. Other important viral diseases are influenza A and B which are caused by influenza A and B virus respectively. Another important common viral disease is viral hepatitis and especially hepatitis B virus infections are widely spread. Effective and selective antiviral agents are needed for the treatment of these diseases.

Several different viruses of both DNA and RNA type have been shown to cause tumors in animals. The effect of cancerogenic chemicals can on animals result in activation of latent tumor viruses. It is possible that tumor viruses are involved in human tumors. The most likely human cases known today are leucemias, sarcomas, breast carcinomas, Burkitt lymphomas, nasopharyngeal carcinomas and cervical cancers where RNA tumor viruses and herpes viruses are indicated. This makes the search for selective inhibitors of tumorogenic viruses and their functions an important undertaking in the effors to treat cancer.

A most important common feature of the interaction between viruses and cells is the replication or transcription of the specific viral genetic information carried by viral nucleic acids. These viral nucleic acids are of two kinds, deoxyribonucleic acids (DNA) or ribonucleic acids (RNA). The primary genetic information of the cell is carried by cell DNA. DNA and RNA synthesis involves complex enzymes called DNA and RNA polymerases respectively. The genetic information is transferred to the new nucleic acid from a template nucleic acid. There are four general ways in which these nucleic acids can be replicated or transcribed.

1. DNA (template) $\xrightarrow{\text{DNA-dependent DNA polymerase}}$ DNA

2. RNA (template) $\xrightarrow{\text{RNA-dependent RNA polymerase}}$ RNA

3. DNA (template) $\xrightarrow{\text{DNA-dependent RNA polymerase}}$ RNA

4. RNA (template) $\xrightarrow{\text{RNA-dependent DNA polymerase}}$ DNA
   (reverse transcriptase)

Processes 1 and 3 are used by cells. DNA viruses such as herpesviruses also use process 1 but the enzyme is different from that of the cell. RNA viruses such as influenza virus use process 2 and the RNA tumor viruses (retroviruses) can transcribe its RNA to DNA according to process 4.

The viral polymerases and the viral nucleic acid syntheses are essential not only for ordinary (productive) virus infections but also for viral transformation of cells to a neoplastic state leading to cancer (tumorogenic function of virus). In the latter case DNA produced by DNA viruses such as herpesvirus or transcribed from RNA tumor viruses and which carries the genetic information for cell transformation can be integrated into the host cell DNA. This integration, or later acts as a consequence of integration (such as interaction with cancerogenic chemicals), can then lead to the transformation of the host cell. The implications of inhibiting reverse transcriptase for cell transformation are also described in U.S. Pat. No. 3,979,511.

Since the viral polymerases in most cases differ from the cellular ones these viral enzymes and viral nucleic acid syntheses are good targets for specific antiviral chemotherapy including chemotherapy of cancer caused by viruses. It should be noted that many compounds presently used for chemotherapy of cancer are inhibitors of nucleic acid synthesis. It is therefore possible that antiviral compounds which are also inhibitors of nucleic acid synthesis can affect tumor cells directly. There is a need for an effective antiviral agent preferably having a selective inhibiting effect on a specific viral function of the virus to be combatted. It is, therefore, a general object of the present invention to provide a novel method for combatting virus infections using an antiviral agent which exerts a selective inhibiting effect on viral functions but which exerts only a negligible inhibiting effect on functions of the host cells.

THE INVENTION

It has been found according to the present invention that the compounds of the formula $$R_1O-\overset{O}{\underset{|}{\underset{OR_2}{P}}}-\overset{O}{\overset{||}{C}}-R_3 \qquad \text{I}$$

wherein $R_1$, $R_2$ and $R_3$ are the same or different, and each is selected from from the group consisting of hydrogen and phenyl groups of the formula

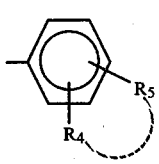

wherein $R_4$ and $R_5$ are the same or different and each is selected from the group consisting of hydrogen, halogen, alkyl having 1, 2, or 3 carbon atoms, alkoxy having 1, 2, or 3 carbon atoms, alkoxycarbonyl having 2-7 carbon atoms; and alkylcarbonyl groups having 2-7 carbon atoms; or $R_4$ and $R_5$ together form a straight saturated alkylene chain having 3 or 4 carbon atoms and being bound to adjacent positions, i.e. 2,3- or 3,4- in the phenyl ring; provided that one of $R_1$ and $R_2$ is a phenyl group of the formula II when $R_3$ is H; and physiologically acceptable salts thereof, inhibit certain viral functions including tumorogenic functions and the multiplication of viruses.

The compounds of the formula I and physiologically acceptable salts thereof are useful in therapeutic and/or prophylactiv treatment of viral diseases and may be useful in therapeutic and/or prophylactic treatment of cancer caused by viruses.

It is understood that the reference to "physiologically acceptable salts" of the compounds of the formula I in the present specification and claims relates only to such compounds which can form salts. Compounds wherein at least one of $R_1$, $R_2$ and $R_3$ is hydrogen can form salts. Compounds wherein all of $R_1$, $R_2$ and $R_3$ are different from hydrogen do not form salts.

Since the compounds of the formula I, when $R_1$ and $R_2$ are different, contain an asymmetric center, they exist in the form of optically active forms, and can be resolved into their optical antipodes by known methods.

In this specification, the compounds of the invention are named as derivatives of the compound hydroxycarbonylphosphonic acid, which compound also is known under the name phosphonoformic acid.

The provision in the definition of the compounds of the invention means that the radicals $R_1$, $R_2$ and $R_3$ in formula I can be combined as illustrated in the following tabulation. It is understood that $R_1$ and $R_2$, which are the same or different, are considered as equivalent and interchangeable in the table below.

| $R_1$ | $R_2$ | $R_3$ |
| --- | --- | --- |
| H | phenyl group of formula II | H |
| phenyl group of formula II | phenyl group of formula II | phenyl group of formula II |
| H | phenyl group of formula II | phenyl group of formula II |
| H | H | phenyl group of formula II |

The compounds of the formula I and physiologically acceptable salts thereof are useful in therapeutic and/or prophylactic treatment of viral diseases and may be useful in therapeutic and/or prophylactic treatment of cancer caused by viruses.

PRIOR ART

Various esters of phosphonoformic acid are described in for example U.S. Pat. Nos. 3,943,201, 3,155,597, 3,533,995 and in Chem. Ber. 57, P 1023 (1924). However, these esters have not been suggested for any pharmacological use. Moreover, the chemical structure of the esters of the present invention is different from that of the prior known esters. More particularly, the novel esters are exclusively esters of phenols.

DETAILED DESCRIPTION OF THE INVENTION

The present invention provides

A. A method for the treatment of diseases caused by viruses in animals including man, comprising administering to an animal so infected a therapeutically effective amount of a compound of the formula I or a physiologically acceptable salt thereof.

B. A method for the treatment of virus-induced neoplastic diseases in animals including man, by inhibiting the transformation of virus-infected cells, characterized by administering to an animal so infected a therapeutically effective amount of a compound of the formula I or a physiologically acceptable salt thereof.

C. A method for the treatment of diseases caused by viruses in animals including man, by inhibiting the activity of viral polymerase, characterized by administering to an animal so infected a compound of the formula I or a physiologically acceptable salt thereof in an amount effective for inhibiting the activity of said viral polymerase.

D. A method for inhibiting the activity of reverse transcriptases of viruses in animals including man, by administration to an animal a compound of the formula I or a physiologically acceptable salt thereof in an amount sufficient for inhibiting the activity of said reverse transcriptase. Particular reverse transcriptases are the reverse transcriptases of retroviruses, such as visna, sarcoma and leucemia viruses.

E. A method for inhibiting the multiplication of virus, in particular herpesviruses, influenza virus and hepatitis B virus, and retroviruses in animals including man, by administering to an animal in need of such treatment a compound of the formula I or a physiologically acceptable salt thereof in an amount sufficient for inhibiting said multiplication.

F. A method for inhibiting the growth of virus-transformed cells in animals including man, characterized by administering to an aminal in need of such treatment a compound of the formula I or a physiologically acceptable salt thereof in an amount sufficient for inhibiting said growth.

G. A method for the treatment of virus-induced neoplastic diseases in animals including man, by inhibiting the multiplication of tumor viruses, characterized by administering to an animal in need of such treatment a compound of the formula I or a physiologically acceptable salt thereof in an amount sufficient for inhibiting such multiplication.

H. A method for the treatment of virusinduced neoplastic diseases in animals including man by inhibiting the activity of reverse transcriptase, characterized by administering to an animal so infected a compound of the formula I or a physiologically acceptable salt thereof in an amount effective for inhibiting the activity of said reverse transcriptase.

I. A method for the treatment of neoplastic diseases in animals including man, characterized by administering to a animal a therapeutically effective amount of phosphonoformic acid or a physiologically acceptable salt thereof.

The invention also relates to the use of a compound of the formula I or a physiologically acceptable salt thereof, in each of the above given methods, A, B, C, D, E, F, G, H, and I. For example, the invention relates to the use of a compound of the formula I or a physiologically acceptable salt thereof, for (a) inhibiting the replication of virus in animals including man, in particular herpesvirus, influenza virus and hepatitis B viruses, and (b) for inhibiting the growth of virus-transformed cells in animals including man.

Furthermore, the invention provides pharmaceutical preparations comprising as active ingredient a compound of the formula I or a physiologically acceptable salt thereof, optionally in association with a pharmaceutically acceptable carrier. The invention also encompasses a process for the preparation of a medicine having antiviral activity, characterized in that a compound of the formula I or a physiologically acceptable salt thereof is brought into an administration form suitable for therapeutical purposes, and the shaped medicine obtained by such process.

The compounds within the formula I are novel compounds, The invention also comprises the novel compounds per se.

The compounds of the formula I may be hydrolyzed in vivo to give phosphonoformic acid or ionized forms thereof, which are antiviral agents. In a more generalized aspect the invention includes within its scope the use of all physiologically acceptable compounds (including physiologically acceptable salts thereof) of the formula I, wherein $R_1$, $R_2$ and $R_3$ when they are different from H, is any pharmaceutically acceptable organic group, which by in vivo hydrolysis is capable of forming phosphonoformic acid or a physiologically acceptable salt thereof in the animal body (i.e. bioprecursors to phosphonoformic acid) for the treatment of virus infections and related ailments, as previously described, in animals including man, and pharmaceutical compositions containing such compounds.

Phosphonoformic acid and physiologically acceptable salts thereof inhibit viral functions such as polymerases including reverse transcriptase and virus multiplication, and have effects on virus infections and virus-related tumors in animal models. The antiviral effects of trisodium phosphonoformate is described by Helgstrand et al. Science 201, 819 (1978).

An important aspect of the invention is that the radicals $R_1$, $R_2$ and $R_3$ in formula I can be chosen in such a way that the compounds of formula I and physiologically acceptable salts thereof possess more favourable pharmacokinetic properties than phosphonoformic acid and physiologically acceptable salts thereof. Such favourable pharmacokinetic properties include better tissue penetration, better oral absorption and prolonged activity.

Although the present invention relates broadly to a novel method for selectively combatting viral diseases in animals and man, and pharmaceutical preparations to be used in such treatment, it will be particularly useful in the treatment of herpesvirus infections, influenza virus infections, hepatitis B virus infections and cancer caused by herpesviruses and RNA tumor viruses.

An especially important area of use for the compositions of the present invention is in the treatment of herpes virus infections. Among the herpesviruses may be mentioned Herpes simplex type 1 and 2, varicella (Herpes zoster), virus causing infectious mononucleosis (i.e. Epstein-Barr virus), and cytomegalovirus. Important diseases caused by herpes viruses are herpes dermatitis, (including herpes labialis), herpes genitalis, herpes keratitis and herpes encephalitis. An other important area of use for the compositions of the present invention is in the treatment of infections caused by orthomyxoviruses, i.e. influenza viruses of type A and type B. A further area of use is the treatment of infections caused by viruses such as hepatitis virus A and hepatitis virus B, papillomaviruses, adenoviruses and poxviruses.

Other possible areas of use for the compositions of the present invention are in the treatment of infections caused by picornaviruses, togaviruses including arboviruses, retroviruses (e.g. leucoviruses), arenaviruses, coronaviruses, rhabdoviruses, paramyxoviruses, hepatitis non A and non B virus, iridoviruses, papovaviruses, parvoviruses, reoviruses. and bunyaviruses.

Another possible area of use for the compositions of the present invention is in the treatment of cancer and tumors, particularly those caused by viruses. This effect may be obtained in different ways, i.e. by inhibiting the transformation of virus-infected cells to a neoplastic state, by inhibiting the spread of viruses from transformed cells to other normal cells and by arresting the growth of virus-transformed cells. A particular area of use for the compositions of the present invention is in the inhibition of reverse transcriptases of RNA tumor viruses. The viruses in this group include all of the transforming sarcoma C-type viruses, the leucemia C-type viruses and the mammary B-type viruses. Possible areas of use for the compositions of the present invention with respect to cancer chemotherapy are treatment of leucemias, lymphomas including Burkitt lymphomas and Hodgkin's disease, sarcomas, breast carcinoma, nasopharyngeal carcinomas and cervical cancers in which RNA tumor viruses and herpesviruses are indicated. Other possible areas of use for the composition of the present invention with respect to cancer chemotherapy are treatment of multiple myeloma and cancer of the lungs (and bronchus), the stomach, the liver, the colon, the bladder, the lips, the bones, the kidneys, the ovary, the prostate, the pancreas, the skin (melanoma), the rectum, the salivary glands, the mouth, the esophagus, the testis, the brain (and cranial meninges), the thyroid gland, the gallbladder (and ducts), the nose, the larynx, connective tissues, the penis, the vulvas, the vagina, the corpus uteri, the tongue, the breasts, and the cervix. Illustrative examples of the meanings of the radicals $R_1$, $R_2$, and $R_3$ in the formula I above are: substituted phenyl:

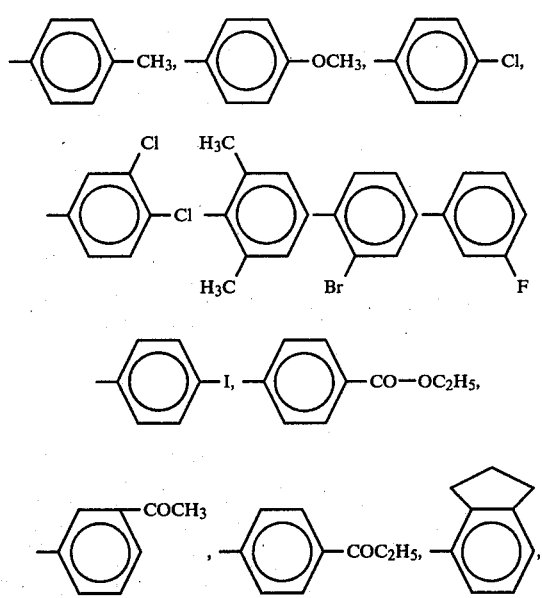

-continued

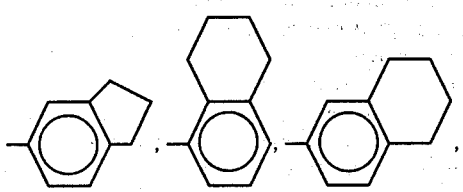

phenyl, 1-adamantyl, 2-adamantyl.

The above illustrative examples are intended to illustrate the meanings of all the radicals $R_1$, $R_2$ and $R_3$ within the boundaries with regard to number of carbon atoms which may be prescribed for each radical.

Preferred groups of the radicals $R_1$ and $R_2$ are:
1. Phenyl
2. monosubstituted phenyl groups
3. disubstituted phenyl groups
4. mono-alkyl substituted phenyl groups
5. mono-halogen substituted phenyl groups
6. mono-alkoxy substituted phenyl groups
7. mono-alkylcarbonyl substituted phenyl groups
8. mono-alkoxycarbonyl substituted phenyl groups
9. di-alkyl substituted phenyl groups
10. di-halogen substituted phenyl groups
11. di-alkoxy substituted phenyl groups
12. alkyl and halogen substituted phenyl groups
13. alkyl and alkoxycarbonyl substituted phenyl groups
14. alkoxy and alkylcarbonyl substituted phenyl groups
15. phenyl groups of the formula

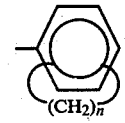

wherein n is 3 or 4 and wherein the alkylene chain is bound to adjacent positions, i.e. 2,3- or 3,4- in the phenyl ring.

Particularly preferred groups of the radicals $R_1$ and $R_2$ are unsubstituted, monosubstituted and disubstituted phenyl groups within the above formula

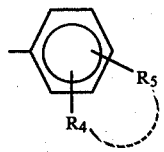

wherein $R_4$ and $R_5$ have the meanings given above.

In a preferred embodiment, $R_1$ and $R_2$ have the same meaning.

Preferred groups of the radical $R_3$ are:
1. Phenyl
2. monosubstituted phenyl groups
3. disubstituted phenyl groups
4. mono-alkyl substituted phenyl groups
5. mono-halogen substituted phenyl groups
6. mono-alkoxy substituted phenyl groups
7. mono-alkylcarbonyl substituted phenyl groups
8. mono-alkoxycarbonyl substituted phenyl groups
9. di-alkyl substituted phenyl groups
10. di-halogen substituted phenyl groups
11. di-alkoxy substituted phenyl groups
12. phenyl groups of the formula

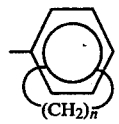

wherein n is 3 or 4 and wherein the alkylene chain is bound to adjacent positions, i.e. 2,3- or 3,4- in the phenyl ring.
13. alkyl and halogen substituted phenyl groups
14. alkyl and alkoxycarbonyl substituted phenyl groups
15. alkoxy and alkylcarbonyl substituted phenyl groups Particularly preferred groups of the radical $R_3$ are unsubstituted, monosubstituted and disubstituted phenyl groups within the above formula

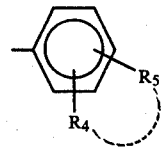

wherein $R_4$ and $R_5$ have the meanings given above.
Preferred combinations of $R_1$, $R_2$ and $R_3$ are:
1. $R_1$, $R_2$ and $R_3$ are phenyl,
2. $R_1$ and $R_2$ are the same of different and are selected from the group consisting of an unsubstituted, monosubstituted or disubstituted phenyl groups within the formula

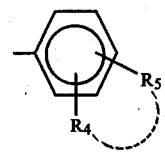

wherein $R_4$ and $R_5$ have the meanings given above, and $R_3$ is phenyl,
3. $R_1$, $R_2$ and $R_3$ are selected from the group consisting of unsubstituted, monosubstituted or disubstituted phenyl groups within the formula

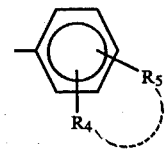

wherein $R_4$ and $R_5$ have the meanings given above,
4. $R_1$ and $R_2$ are hydrogen and $R_3$ is phenyl,
5. $R_1$ and $R_2$ are hydrogen and $R_3$ is selected from the group consisting of monosubstituted phenyl groups,
6. $R_1$ and $R_2$ are hydrogen and $R_3$ is selected from the group consisting of disubstituted phenyl groups,
7. $R_1$ and $R_2$ are hydrogen and $R_3$ is selected from the group consisting of mono-alkyl substituted phenyl groups, 8. $R_1$ and $R_2$ are hydrogen and $R_3$ is selected from the group consisting of mono-halogen substituted phenyl groups, 9. $R_1$ and $R_2$ are hydrogen and $R_3$ is selected from the group consisting of mono-alkoxy substituted phenyl groups, 10. $R_1$ and $R_2$ are hydrogen and $R_3$ is selected from the group consisting of mono-alkoxycarbonyl substituted phenyl groups, 11. $R_1$ and $R_2$ are hydrogen and $R_3$ is selected from the groups consisting of mono-alkylcarbonyl substituted phenyl groups, 12. $R_1$ and $R_2$ are hydrogen and $R_3$ is selected from the groups consisting of di-alkyl substituted phenyl groups, 13. $R_1$ and $R_2$ are hydrogen and $R_3$ is selected from the group consisting of di-halogen substituted phenyl groups, 14. $R_1$ and $R_2$ are hydrogen and $R_3$ is selected from the group consisting of di-alkoxy substituted phenyl groups, 15. $R_1$ and $R_2$ are hydrogen and $R_3$ is selected from the group consisting of phenyl groups of the formula

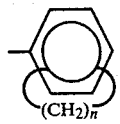

wherein n is 3 or 4 and wherein the alkylene chain is bound to adjacent positions, i.e. 2,3- or 3,4- in the phenyl ring, 16. $R_1$ is hydrogen and $R_2$ and $R_3$ are phenyl, 17. $R_1$ is hydrogen, $R_2$ is monosubstituted or disubstituted phenyl groups within the formula

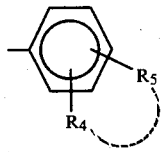

wherein $R_4$ and $R_5$ have the meanings given above and $R_3$ is phenyl,

18. $R_1$ is hydrogen and $R_2$ and $R_3$ are the same or different and are selected from the group consisting of monosubstituted or disubstituted phenyl groups within the formula

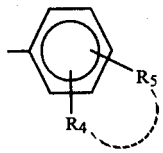

wherein $R_4$ and $R_5$ have the meanings given above,

19. $R_1$ is hydrogen, $R_2$ is phenyl and $R_3$ is selected from the group consisting of monosubstituted or disubstituted phenyl groups within the formula

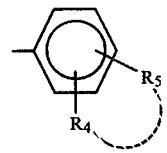

wherein $R_4$ and $R_5$ have the meanings given above.

20. $R_1$ is hydrogen, and $R_2$ and $R_3$ are the same or different and are selected from the group consisting of unsubstituted, monosubstituted or disubstituted phenyl groups within the formula

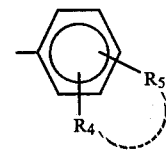

wherein $R_4$ and $R_5$ have the meanings given above,

21. $R_1$ and $R_3$ are hydrogen and $R_2$ is phenyl,

22. $R_1$ and $R_3$ are hydrogen and $R_2$ is selected from the group consisting om monosubstituted phenyl groups, 23. $R_1$ and $R_3$ are hydrogen and $R_2$ is selected from the group consisting of disubstituted phenyl groups, 24. $R_1$ and $R_3$ are hydrogen and $R_2$ is selected from the group consisting of mono-alkyl substituted phenyl groups, 25. $R_1$ and $R_3$ are hydrogen and $R_2$ is selected from the group consisting of mono-halogen substituted phenyl groups, 26. $R_1$ and $R_3$ are hydrogen and $R_2$ is selected from the group consisting of mono-alkoxy substituted phenyl groups, 27. $R_1$ and $R_3$ are hydrogen and $R_2$ is selected from the group consisting of mono-alkoxycarbonyl substituted phenyl groups, 28. $R_1$ and $R_3$ are hydrogen and $R_2$ is selected from the group consisting of mono-alkylcarbonyl substituted phenyl groups, 29. $R_1$ and $R_3$ are hydrogen and $R_2$ is selected from the group consisting of di-alkyl substituted phenyl groups, 30. $R_1$ and $R_3$ are hydrogen and $R_2$ is selected from the group consisting of di-halogen substituted phenyl groups, 31. $R_1$ and $R_3$ are hydrogen and $R_2$ is selected from the group consisting of di-alkoxy substituted phenyl groups, 32. $R_1$ and $R_3$ are hydrogen and $R_2$ is selected from the group consisting of phenyl groups of the formula

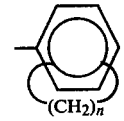

wherein n is 3 or 4 and wherein the alkylene chain is bound to adjacent positions, i.e. 2,3- or 3,4- in the phenyl ring, 33. compounds of the formula I wherein $R_1$ and $R_2$ are hydrogen, 34. compounds of the formula I wherein $R_1$ is hydrogen, 35. compounds of the formula I wherein $R_1$ and $R_3$ are hydrogen, Examples of compounds of the invention are given in the following table.

| $R_1$ | $R_2$ | $R_3$ |
|---|---|---|
| H | H | phenyl |
| H | H | 4-methylphenyl |
| H | H | 4-methoxyphenyl |
| H | H | 4-chlorophenyl |
| H | H | 3,4-dichlorophenyl |
| H | H | 4-ethoxycarbonylphenyl |
| H | phenyl | phenyl |
| H | 4-chlorophenyl | phenyl |
| H | 3,4-dichlorophenyl | phenyl |
| H | 4-methoxyphenyl | phenyl |
| H | 4-methylphenyl | phenyl |
| H | 4-ethoxycarbonylphenyl | phenyl |
| H | phenyl | 4-chlorophenyl |
| H | phenyl | 3,4-dichlorophenyl |
| H | phenyl | 4-methoxyphenyl |
| H | phenyl | 4-methoxyphenyl |
| H | phenyl | 4-ethoxycarbonylphenyl |
| H | 4-chlorophenyl | 4-methoxyphenyl |
| H | 4-chlorophenyl | 4-methoxyphenyl |
| H | 4-chlorophenyl | 4-ethoxycarbonylphenyl |
| H | 4-chlorophenyl | 5-indanyl |
| H | 4-methoxyphenyl | 4-methoxyphenyl |
| H | 4-methoxyphenyl | 4-ethoxycarbonylphenyl |
| H | 4-methoxyphenyl | 5-indanyl |
| H | 4-methylphenyl | 4-chlorophenyl |
| H | 4-methylphenyl | 4-methoxyphenyl |
| H | 4-methylphenyl | 4-ethoxycarbonylphenyl |
| phenyl | phenyl | phenyl |
| H | phenyl | H |
| H | 4-methylphenyl | H |
| H | 4-methoxyphenyl | H |
| H | 4-chlorophenyl | H |
| H | 3,4-dichlorophenyl | H |
| H | 4-ethoxycarbonylphenyl | H |
| H | H | 2,6-dimethylphenyl |
| H | H | 5-indanyl |
| H | H | 4-acetylphenyl |
| H | 2,6-dimethylphenyl | phenyl |
| H | 5-indanyl | phenyl |
| H | 4-acetylphenyl | phenyl |
| H | 2,6-dimethylphenyl | H |
| H | 5-indanyl | H |
| H | 4-acetylphenyl | H |

Particularly preferred compounds are:

| $R_1$ | $R_2$ | $R_3$ | Code |
|---|---|---|---|
| H | H | 4-methylphenyl | VIS 130 |
| H | H | 4-methoxyphenyl | VIS 239 |
| H | H | 4-chlorophenyl | VIS 238 |
| H | H | 3,4-dichlorophenyl | VIS 135 |
| H | phenyl | phenyl | VIS 046 |
| H | 4-methoxyphenyl | phenyl | VIS 058 |
| H | 4-chlorophenyl | phenyl | VIS 063 |
| phenyl | phenyl | phenyl | VIS 040 |
| 4-methylphenyl | 4-methylphenyl | phenyl | VIS 056 |
| H | phenyl | H | VIS 041 |
| H | 4-methylphenyl | H | VIS 059 |
| H | 4-methoxyphenyl | H | VIS 067 |
| H | 4-chlorophenyl | H | VIS 066 |
| H | H | phenyl | VIS 412 |
| H | H | 4-ethoxycarbonylphenyl | VIS 242 |
| H | 4-methylphenyl | phenyl | VIS 065 |
| H | 2,6-dimethylphenyl | H | VIS 440 |
| H | 5-indanyl | H | VIS 442 |
| H | 4-acetylphenyl | H | VIS 073 | and physiologically acceptable salts thereof.

Salts of the active substances

Physiologically acceptable salts of those active substances of the formula in which form salts are prepared by methods known in the art as illustrated in the following.

Examples of metal salts which can be prepared are salts containing Li, Na, K, Ca, Mg, Zn, Mn and Ba. A less soluble metal salt can be precipitated from a solution of a more soluble salt by addition of a suitable metal compound. Thus for examples, Ca, Ba, Zn, Mg, and Mn salts of the active substances can be prepared from sodium salts thereof. The metal ion of a metal salt of the active substances can be exchanged by hydrogen ions, other metal ions, ammonium and ammonium ions substituted by one or more organic radicals by using a cation exchanger.

Examples of other useful salts which can be prepared in this way are the salts of the formula $$\left[ R_3O-\overset{O}{\underset{\underset{OR_2}{|}}{C}}-\overset{O}{\overset{\|}{P}}-OR_1 \right] [X]_n \quad III$$

in which formula $R_1$, $R_2$ and $R_3$ has the same meaning as above, n is 1 or 2, and X is a salt-forming component such as $NH_3$, $CH_3NH_2$, $C_2H_5NH_2$, $C_3H_7NH_2$, $C_4H_9NH_2$, $C_5H_{11}NH_2$, $C_6H_{13}NH_2$, $(CH_3)_2NH$, $(C_2H_5)_2NH$, $(C_3H_7)_2NH$, $(C_4H_9)_2NH$, $(C_5H_{11})_2NH$, $(C_6H_{13})_2NH$, $(CH_3)_3N$, $(C_2H_5)_3N$, $(C_3H_7)_3N$, $(C_4H_9)_3N$, $(C_5H_{11})_3N$, $(C_6H_{13})_3N$, $C_6H_5CH_2NH_2$, $HOCH_2CH_2NH_2$, $(HOCH_2CH_2)_2NH$, $(HOCH_2CH_2)_3N$, $C_2H_5NH(CH_2CH_2OH)$, $C_2H_5N(CH_2CH_2OH)_2$, $(HOH_2C)_3CNH_2$ and morpholine Further examples of other useful salts which can be prepared by the ion exchange technique are quaternary ammonium salts of the active substances, i.e. salts in which the hydrogens in the active substances (structural formula I) have been substituted with quarternary ammonium ions such as $(CH_3)_4N$, $(C_3H_7)_4N$, $(C_4H_9)_4N$, $(C_5H_{11})_4N$, $(C_6H_{13})_4N$ and $C_2H_5N(CH_2CH_2OH)_3$. Lipophilic salts of this type can also be prepared by mixing a salt of the active substances with a quaternary ammonium salt in water and extracting out the resulting quaternary ammonium salt of the active substances with an organic solvent such as dichloromethane, chloroform, ethyl acetate and methyl isobutyl ketone.

The compounds utilized within the invention may be formulated for use in human and veterinary medicine for therapeutic and prophylactic use. The compounds may be used in the form of a physiologically acceptable salt. Suitable salts are e.g. amine salts, e.g. dimethylamine and triethylamine salt, ammonium salt tetrabutylammonium salt, cyclohexylamine salt, dicyclohexylamine salt; and metal salts, e.g. mono-, and disodium salt, mono- and dipotassium salt, magnesium salt, calcium salt and zinc salt.

The compounds utilized within the invention are particularly useful for systemic treatment of virus infections, by oral administration or by injection. In comparison with phosphonoformic acid, they are generally more stable in acid solutions, and are thus less readily decomposed in the stomach.

In comparison with phosphonoformic acid the compounds of the present invention are more lipophilic and are thus more suitable to treat virus infections in organs for which penetration through lipid barriers are of importance.

In clinical practice the compound will normally be administered topically, orally, intranasally, by injection or by inhalation in the form of a pharmaceutical preparation comprising the active ingredient in the form of the original compound or optionally in the form of pharmaceutically acceptable salt thereof, in association with a pharmaceutically acceptable carrier which may be a solid, semi-solid or liquid diluent or an ingestible capsule, and such preparations comprise a further aspect of the invention. The compound may also be used without carrier material. As examples of pharmaceutical preparations may be mentioned tablets, drops such as nasal and eye drops, preparations for topical application such as ointments, jellies, creams and suspensions, aerosols for inhalation, nasal spray, liposomes, etc. Usually the active substance will comprise between 0.05 and 99, or between 0.1 and 99% by weight of the preparation, for example between 0.5 and 20% for preparations intended for injection and between 0.1 and 50% for preparations intended for oral administration.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax ® or other polyethylene glycol waxes and compressed to form tablets or cores for dragees. If dragees are required, the cores may be coated for example with concentrated sugar solutions which may contain gum arabic, talc and/or titainium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsules, the active substance may be admixed with a Carbowax ® or a suitable oil as e.g. sesam oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as a physiologically inert plastic substance.

In order to obtain dosage units of oral preparations—tablets, capsules, etc.—which are designed so as to prevent release of and possible decomposition of the active substance in the gastric juice, the tablets, dragees etc. may be enteric coated, that is provided with a layer of a gastric juice resistant enteric film or coating having such properties that it is not dissolved at the acidic pH in the gastric juice. Thus, the active substance will not be released until the preparation reaches the intestines. As examples of such known enteric coatings may be mentioned cellulose acetate phthalate, hydroxypropylmethylcellulose phthalates such as those sold under the trade names HP 55 and HP 50, and Eudragit ®L and Eudragit ®S.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbic acid, and citric acid, and for example aroma.

Liquid preparations for oral application may be in the form of elixirs, syrups or suspensions, for example solutions containing from about 0.1% to 20% by weight of active substance, sugar and a mixture or ethanol, water, glycerol, propylene glycol and optionally aroma, saccharine and/or carboxymethylcellulose as a dispersing agent.

For parenteral application by injection preparations may comprise an aqueous suspension of the active compounds according to the invention, desirably in a concentration of 0.5–10%, and optionally also a stabilizing agent and/or buffer substances in aqueous solution. Dosage units of the solution may advantageously be enclosed in ampoules.

For topical application, especially for the treatment of herpes virus infections on skin, genitals and in mouth and eyes the preparations are suitably in the form of a solution, ointment, gel, suspension, cream or the like. The amount of active substance may vary, for example between 0.05–20% by weight of the preparation. Such preparations for topical application may be prepared in known manner by mixing the active substance with known carrier materials such as isopropanol, glycerol, paraffine, stearyl alcohol, polyethylene glycol, etc. The pharmaceutically acceptable carrier may also include a known chemical absorption promoter. Examples of absorption promoters are e.g. dimethylacetamide (U.S. Pat. No. 4,472,931), trichloroethanol or trifluoroethanol (U.S. Pat. No. 3,891,757), certain alcohols and mixtures thereof (British Pat. No. 1,001,949). A carrier material for topical application to unbroken skin is also described in the British patent specification No. 1,464,975, which discloses a carrier material consisting of a solvent comprising 40–70% (v/v) isopropanol and 0–60% (v/v) glycerol, the balance, if any, being an inert constituent of a diluent not exceeding 40% of the total volume of solvent.

The dosage at which the active ingredients are administered may vary within a wide range and will depend on various factors such as for example the severity of the infection, the age of the patient, etc., and may have to be individually adjusted. As a possible range for the amount of the active substance which may be administered per day may be mentioned from about 0.1 mg to about 2000 mg or from about 1 mg to about 2000 mg, or preferably from 1 mg to about 2000 mg for topical administration, from 50 mg to about 2000 mg or from 100 to 1000 mg for oral administration and from 10 mg to about 2000 mg or from 50 to 500 mg for injection. In severe cases it may be necessary to increase these doses 5-fold to 10-fold. In less severe cases it may be sufficient to use up to 500 or 1000 mg.

The pharmaceutical compositions containing the active ingredients may suitably be formulated so that they provide doses within these ranges either as single dosage units or as multiple dosage units.

Thus, it has been found according to the invention that the above compounds, and the physiologically acceptable salts thereof can be used to selectively inhibit the multiplication of viruses and the compounds and physiologically acceptable salts thereof are therefore useful in therapeutic and/or propylactic treatment of virus infections and neoplastic diseases, as described above.

The hydroxycarbonylphosphonic acid triesters may be prepared by known methods for example as described in Houben-Weyl, Methoden der Organischen Chemie, Auflage 4, Band XII, Teil 1, Organische Phosphorverbindungen, s. 433–463. Examples of such methods are the following.

Reference to "meaning given above" for $R_1$ $R_2$ and $R_3$ as used below refers to the definitions given in formula I.

A. Reacting formic acid ester compounds with phosphite triesters according to the formula:

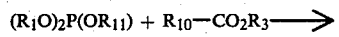

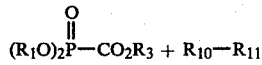

wherein $R_1$ and $R_2$ have the meaning given above, $R_{10}$ is a leaving group suitable for Arbuzow type reactions, such as for example Cl, Br, I, sulphonate, carboxylate, alkoxide, $R_{11}$ may be an alkyl, a cycloalkyl, a cycloalkyl-alkyl, a benzyl, an adamantyl or any phosphite esterifying group suitable for Arbuzow type reactions.

Preferably the reaction is performed at 0° to 150° for 1 to 50 hours.

B. Reacting formic acid ester compounds with phosphite triesters according to the formula:

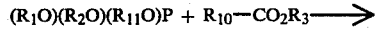

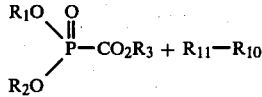

wherein $R_1$, $R_2$, $R_3$, $R_{10}$ and $R_{11}$ have the meaning given above.

C. Reacting formic acid ester compounds with phosphite diester salts according to the formula:

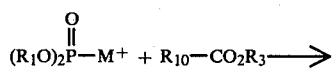

wherein $R_1$, $R_3$ and $R_{10}$ have the meaning given above and $M^+$ is a cation, preferably a metal such as $Li^+$, $Na^+$ or $K^+$, and the reaction is preferably performed at 0° to 100° for 1 to 50 hours in a solvent such as for example, toluene, ether or tetrahydrofurane.

The phosphite diester salts are prepared by treating the phosphite diester with a suitable proton abstracting compound, such as a metal alkoxide, suitably free from alcohol, such as lithium-, sodium- or potassium methoxide, ethoxide or t-butoxide or with a hydride such as sodium- or potassium hydride, or with a base such as butyllithium.

The starting materials used in the above methods of preparation A-C are known compounds, or may be prepared by known methods commonly used for the synthesis of formate esters and phosphite triesters. Example of methods used for the synthesis of haloformate esters may be found in, or referred to in M. Matzner et al. Chem. Rev. 64 (1964), 645. Examples of methods used for the synthesis of phosphite triesters may be found in Houben-Weyl, Methoden der Organischen Chemie, Auflage 4, Band XII, Teil 2, Organische Phosphorverbindungen, P. 5–78.

D. Esterification of the phosphonic acid groups of hydroxycarbonylphosphonic acid monoester according to the formula:

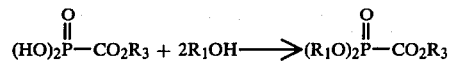

$R_1$ and $R_3$ have the meaning given above. The reaction is performed through the intermediary of activating agents known per se for the phosphorylation of alcohols and phenols. Examples of such methods are described for example by L. A. Slotin in Synthesis 1977, 737 and by H. Seliger and H. Kössel in Progress in the Chemistry of Organic Natural Products 32 (1975) 297.

Synthesis of monoesters of the carboxylic group of hydroxycarbonylphosphonic acid are described below in methods S-W.

E. Esterification of hydroxycarbonylphosphonic acid diesters according to the formula:

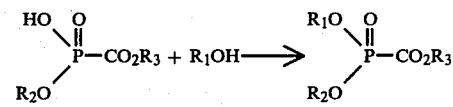

$R_1$, $R_2$ and $R_3$ have the meaning given above.

The reaction is performed through the intermediary of activating agents known per se for the phosphorylation of alcohols and phenols. Examples of such methods are described for example by L. A. Slotin in Synthesis 1977, 737, and by H. Seliger and H. Kössel in Progress in the Chemistry of Organic Natural Products 32 (1975) 297.

Synthesis of hydroxycarbonylphosphonic acid diesters are described below in methods J-N.

F. Reacting oxycarbonylphosphonic acid dihalide esters according to the formula:

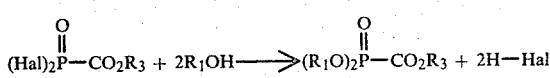

Hal is Cl, Br or I and $R_1$ and $R_2$ have the meaning given above.

The reactions are performed by methods known per se for the phosphorylation of alcohols and phenols by phosphoric and phosphonic acid halides. Examples of such methods are described for example by L. A. Slotin in Synthesis 1977, 737 and by H. Saliger and H. Kössel in Progress in the Chemistry of Organic Natural Products 32 (1975) 297.

The oxycarbonylphosphonic acid dihalide esters are prepared from oxycarbonylphosphonic acid monocarboxylic esters by methods known per se for the synthesis of dihalides of phosphonic acids and phosphonic acids. References for those methods are found for example in the two publications above and in Houben-Weyl, Methoden der Organischen Chemie, Auflage 4, Band XII/1. S. 386–406 and Band XII/2 S. 211–225 and S. 274–292.

Oxycarbonylphosphonic acid monocarboxylic esters are prepared by methods described below in S-W.

G. Reacting oxycarbonylphosphonic acid monohalide diesters according to the formula:

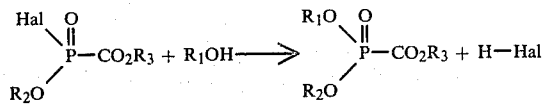

Hal is Cl, Br, or I and $R_1$, $R_2$ and $R_3$ have the meaning given above.

The reaction is performed by methods known per se for the phosphorylation of alcohols and phenols. Examples of such methods are described for example by L. A. Slotin in Synthesis 1977, 737 and by H. Seliger and H. Kössel in Progress in the Chemistry of Organic Natural Products 32 (1975) 297.

Oxycarbonylphosphonic acid monohalide diesters are prepared from oxycarbonylphosphonic acid diesters by methods known per se for the synthesis of monohalides of phosphonic and phosphoric acids. References for those methods are found for example in the two publications above and in Houben-Weyl, Methoden der Organischen Chemie, Auflage 4, Band XII/1, s. 386-406 and Band XII/2 s. 211-225 and s. 274-292.

Oxycarbonylphosphonic acid diesters are prepared by methods described below in J-N.

H. Reacting a carbonylphosphonic acid diester according to the formula:

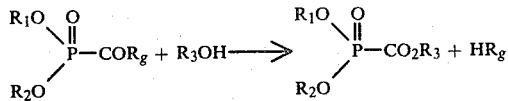

$R_1$, $R_2$ and $R_3$ have the meaning given above and $R_g$ is a suitable activating moiety, known per se as a good leaving group in substitution reactions on activated carboxylic acid groups. Preferably $R_g$ is a group such as for example p-nitrophenoxy or imidazolyl.

The activated carbonylphosphonic acid diester used as a starting material may for example be prepared by methods analogous to those described above in A-C.

Diesters of hydroxycarbonylphosphonic acid are prepared by known methods, such as J. Reacting a hydroxycarbonylphosphonic acid triester with an iodide or a bromide anion, according to the formula:

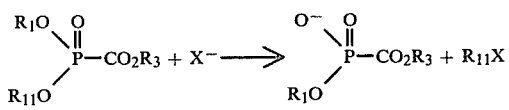

wherein X is Br or I and $R_1$, $R_3$ and $R_{11}$ have the meaning given above.

Preferably the reaction is carried out with sodium iodide in a solvent such as for example tetrahydrofuran or acetone. Preferably the reaction is carried out at a temperature from 20° to 100° from 2 hours to 7 days.

The hydroxycarbonylphosphoric acid triester may be prepared by methods analogous to those described above in A-H.

A similar reaction to obtain the triester, is the following reaction between a phosphite triester and a formic acid ester:

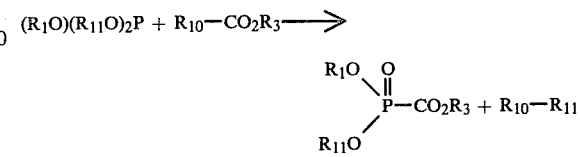

wherein $R_1$, $R_3$, $R_{10}$ and $R_{11}$ have the meaning given above. Preferably the reaction is performed at 20° to 100° from 2 hours to 7 days.

K. Hydrolysing a hydroxycarbonylphosphonic acid triester with a base according to the formula:

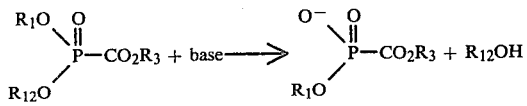

$R_1$ and $R_3$ have the meaning given above. $R_{12}$ is a hydrolyzable phosphate ester group. For example it may have the meaning given $R_1$ and $R_2$ and it may be for example be a more generally substituted aryl group, benzyl or a suitable alkyl group.

Preferably the reaction is carried out with a base such as for example sodium hydrogencarbonate, sodiumcarbonate or sodium hydroxide in water at a temperature from 20° to 100° from 2 hours to 7 days.

The hydroxycarbonylphosphonic acid triester may be prepared by methods analogous to those described above in A-J.

L. Aqueous hydrolysis of hydroxycarbonylphosphonic acid triester, containing one silyl esterified phosphonate group according to the formula:

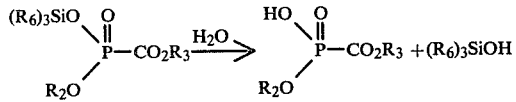

where $R_2$ and $R_3$ have the meaning given above and $R_6$ is an inert organic residue, preferably an organic group such as for example $CH_3$. Another example of silylester groups are for example butyldiphenylsilyl compounds, which have been described by R. A. Jones et al. Biochemistry 17 (1978) 1268 as phosphate ester derivatives.

Optionally the formed phosphonic acid group may be neutralized. Preferably it may be neutralized with a base such as for example $MHCO_3$, $M_2CO_3$ or $MOH$ or with a weak cation exchanger ($M^+$), where $M^+$ is $NH_4^+$ or a metal such $Li^+$, $Na^+$ or $K^+$.

The silyl esterified phosphonate group may be obtained by treating the hydroxycarbonyl phosphonic acid triester with a halosilane according to the formula:

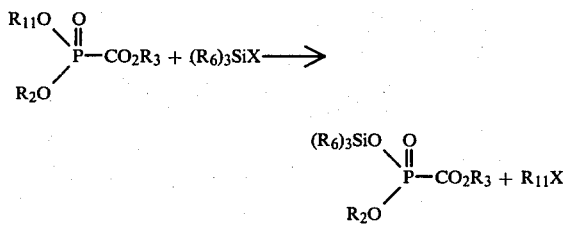

X is Cl, Br or I and $R_2$, $R_3$, $R_6$ and $R_{11}$ have the meaning given above.

Preferably the reagents used for silylation are for example bromotrimethylsilane at $-20°$ to $50°$ for ½ to 20 hours, or alternatively for example chlorotrimethylsilane at $20°$ to reflux temperature for several days.

The hydroxycarbonylphosphonic acid triesters are prepared by methods analogous to those described above in A-J. Alternatively the silyl esterified phosphonate group may be prepared by reacting a phosphite triester containing two silyl ester groups, with a formate ester, according to the formula:

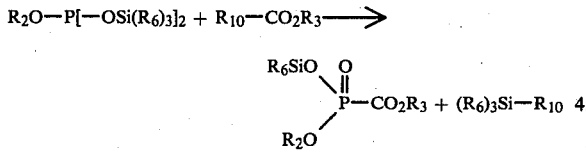

$R_2$, $R_3$, $R_6$ and $R_{10}$ have the meaning given above.

Preferably the phosphite is an ester such as for example a bis-(trimethylsilylated) phosphite triester. These compounds can be prepared by methods known per se. For example the synthesis of propyl- and hexyl-bis-(trimethylsilyl)phosphites are described in T. R. Herrin et al., J. Med, Chem. 20 (1977) 660.

M. Reacting oxycarbonylphosphonic acid monocarbolyic esters according to the formula:

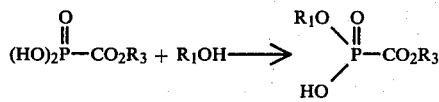

$R_1$ and $R_3$ have the meaning given above. The reaction is performed through the intermediary of activating agents known per se for the phosphorylation of alcohols and phenols. Examples of such methods are described for example by L. A. Slotin in Synthesis 1977, 737 and by H. Seliger and H. Kössel in Progress in the Chemistry of Organic Natural Products 32 (1975) 297.

Synthesis of oxycarbonylphosphonic acid monocarboxylic acids are described below in methods S-W.

N. Reacting hydroxycarbonylphosphonic acid mono-P ester with an esterifying halide, using a tetraalkylammoniumsalt as a catalyst, according to the formula:

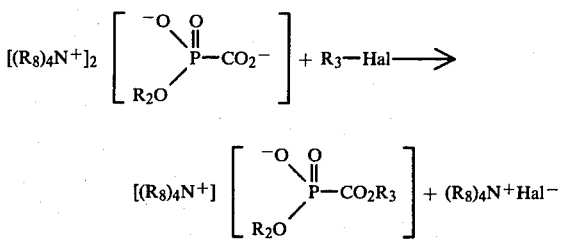

Hal is Cl, Br or I. $R_2$ and $R_3$ have the meaning given above and $R_8$ is an alkyl residue such as for example n-butyl, n-pentyl, n-hexyl, n-heptyl and n-octyl. Preferably n-heptyl is used and preferably the reaction is performed as an extractive alkylation as described by for example.

A. Brändström in Preparative Ion Pair Extraction (Apotekarsocieteten, Hässle, Sweden 1976). Also as described the phosphate group may be transformed to a salt

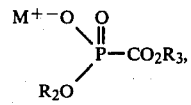

where $M^+$ is for example $NH_4^+$ or a metal such as $Li^+$, $Na^+$ or $K^+$.

The synthesis of hydroxycarbonylphosphonic acid mono-P esters are described below in methods O-R.

Monoesters of the phosphonic group of hydroxycarbonylphosphonic acid are prepared by known methods such as, O. Hydrolyzing a hydroxycarbonylphosphonic acid triester according to the formula:

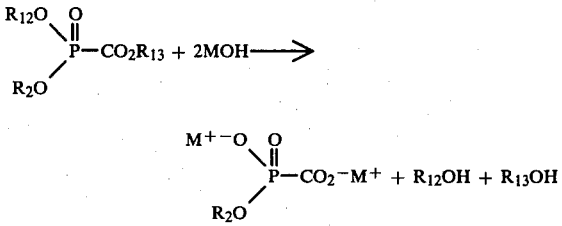

wherein M is a cation such as $NH_4^+$ or $Li^+$, $Na^+$ or $K^+$ and wherein $R_2$ and $R_{12}$ have the meaning given above. $R_{13}$ has the meaning given $R_{12}$, and $R_{12}$ and $R_{13}$ may be the same or different.

Preferably the reaction is carried out in water at $20°$ to $100°$ for 1 to 10 hours.

The hydroxycarbonylphosphonic acid triesters are prepared by methods analogous to those described above in A-J.

P. By the stepwise deesterification of a phosphonic acid trisubstituted silyl ester group, and the carboxylic acid ester group, of hydroxycarbonylphosphonic acid triesters, according to the formula:

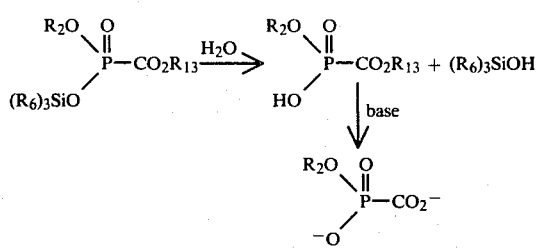

$R_2$, $R_6$ and $R_{13}$ have the meaning given above, and the silyl ester group is preferably a group such as exemplified above in method L.

The trimethylsilyl ester group is preferably hydrolyzed with water and the free acid group is preferably converted to a salt by a weak cation exchanger ($M^+$) or with an aqueous base such as $MHCO_3$, $M_2CO_3$ or MOH.

The carboxylic acid ester group is preferably hydrolyzed in for example water and neutralized with a weak cation exchanger ($M^+$) or with for example an aqueous base such as $MHCO_3$, $M_2CO_3$ or MOH.

$M^+$ is $NH_4^+$ or a metal such as Li, Na, or K.

Compounds containing the silylesterified phosphonate group may be prepared by known methods as described in method L. above.

Q. By the stepwise disterification of the silyl and benzyl ester group of alkyl (or aryl), silyl benzyloxycarbonylphosphonate according to the formula:

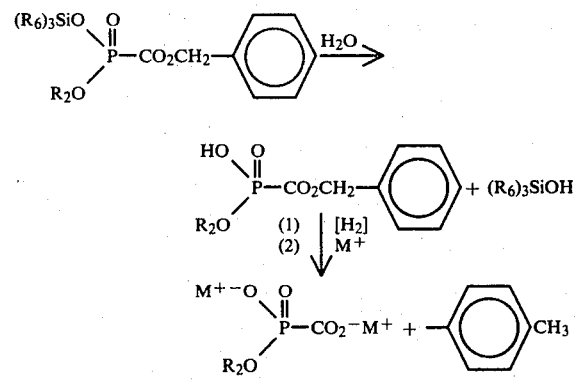

$M^+$ is $NH_4^+$ or a metal such as for example $Li^+$, $Na^+$ or $K^+$, and $R_2$ and $R_6$ have the meaning given above. The silyl ester group is preferably a group such as described above in method L.

The benzyl ester group is preferably hydrogenated with a catalyst such as for example palladiumcarbon. The free acid groups are converted to their metal salts by the treatment with a weak cation exchanger ($M^+$) or with a base such as for example $MHCO_3$, $M_2CO_3$ or MOH.

The silylated compound may be prepared by known methods, analogous to those described above in L.

R. By the deesterification of the bis-silylester groups (on the phosphonic acid on the carboxylic acid groups) of hydroxycarbonylphosphonic acid triesters according to the formula:

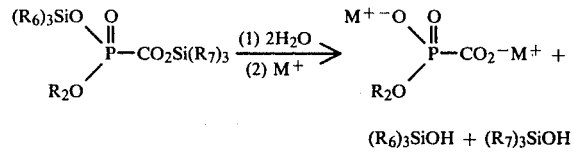

$R_2$ has the meaning given above, $R_6$ and $R_7$ are inert organic residues, the same or different, preferably they are the same and a group such as for example $CH_3$. The silyl ester groups may also be for example butyldiphenylsilyl groups as described above in method L. $M^+$ is $NH_4^+$ or a metal such as $Li^+$, $Na^+$ or $K^+$.

The silyl ester groups are preferably hydrolyzed with for example water and neutralized with for example a weak cation exchanger ($M^+$) or an aqueous base such as $MHCO_3$, $M_2CO_3$ or MOH.

The bis-silylated triester of hydroxycarbonylphosphonic acid may be prepared by methods known per se, according to the formula:

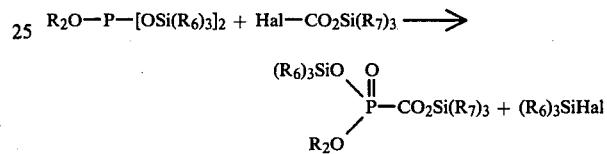

Hal is Cl, Br or I and $R_2$, $R_6$ and $R_7$ have the meaning given above.

Preferably the phosphite is an ester such as for example a bis(trimethylsilylated) phosphite triester. These compounds can be prepared as described above in L.

The haloformate silylesters may be prepared according to the formula:

$$COCl_2 + HOSi(R_7)_3 \rightarrow Cl-CO-Si(R_7)_3 + HCl$$

$R^7$ has the meaning given above.

The reaction is carried out under anhydrous conditions, and preferably a base such as for example N,N-dimethylaniline is used for capturing the released hydrogen chloride. The reaction is preferably carried out in an inert solvent such as for example toluene or ether, at for example $-10°$ to $25°$ for 1 to 25 hours.

Monoesters of the carboxylic group of hydroxycarbonylphosphonic acid are prepared by known methods, such as.

S. Aqueous hydrolysis of a hydroxycarbonylphosphonic acid triester, containing two silyl esterified phosphonate groups, according to the formula:

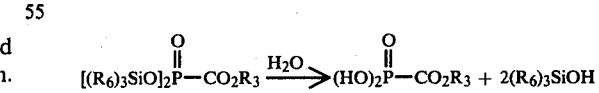

$R_3$ and $R_6$ have the meaning given above. Preferably $R_6$ is for example $CH_3$. The silyl ester derivatives may also be for example butyldiphenylsilyl groups as described above in method L.

Optionally the formed phosphonic acid groups can be neutralized. Preferably they may be neutralized with a weak cation exchanger ($M^+$) or with base such as $MHCO_3$, $M_2CO_3$ or MOH. $M^+$ is $NH_4^+$ or a metal such as $Li^+$, $Na^+$ or $K^+$.

The phosphonate bis-silyl esters may be obtained according to the formula:

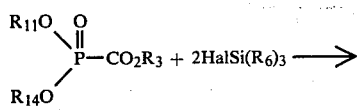

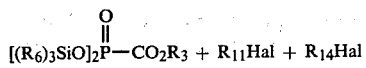

$R_3$, $R_6$ and $R_{11}$ have the meaning given above. $R_{14}$ has the meaning given $R_{11}$ and $R_{11}$ and $R_{14}$ may be the same or different. Preferably the organic residues of the silyl group are as described above. Hal is Cl, Br or I and preferably the reaction is performed at $-20°$ to reflux temperature for 1 hour to several days.

The hydroxycarbonylphosphonic acid triesters are prepared by methods analogous to those described above in A–J.

Another similar way of obtaining the hydroxycarbonylphosphonic acid triester is the reaction according to the following formula:

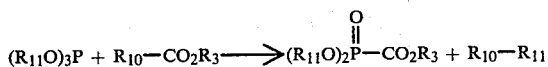

wherein $R_3$, $R_{10}$ and $R_{11}$ have the meaning given above.

Alternatively the bis-silylphosphonate esters may be prepared by reacting a tris-silylphosphite with a formate ester according to the formula:

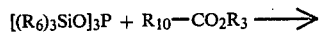

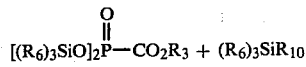

$R_3$, $R_6$ and $R_{10}$ have the meaning given above and preferentially the organic residues of the silyl group are as described above. Preferably the reaction is performed at 20°–150° for 1 to 25 hours.

The tris-silylphosphites are prepared by known methods, as described for example by Herrin et al in J. Med Chem. 20 (1977) 660, for the preparation of tris(trimethylsilyl)phosphite.

T. Reacting triesters of hydroxycarbonylphosphonic acid with hydrohalide acids according to the formula:

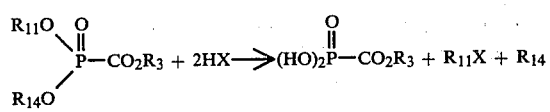

$R_3$, $R_{11}$ and $R_{14}$ have the meaning given above. X is Cl, Br or I.

Preferably HI may be used and the reaction may preferably be performed in a dry solvent such as methylene chloride or acetic acid at a temperature from 0° to 30°. Examples of the reaction may be found in the patents U.S. Pat. No. 3,943,201 and DT-OLS 2435 407.

Optionally the phosphonic acid groups may be neutralized. Preferably a weak cation exchanger (M+) or a base such as $MHCO_3$, $M_2{}^+CO_3$ or MOH is used. M+ is for example $NH_4{}^+$ or a metal such as Li+, Na+ or $K^2$.

The hydroxycarbonylphosphonic acid triester may be prepared by methods analogous to those described above in A–J and S.

U. Hydrogenating dibenzyl, aryloxycarbonylphonates according to the formula:

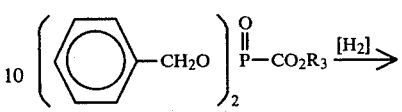

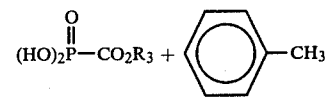

$R_3$ has the meaning given above.

Preferably the reaction may be performed with a catalyst such as palladiumcarbon. Optionally the phosphonic acid groups may be neutralized. Preferably they may be neutralized with a weak cation exchanger (M+) or with a base such as $MHCO_3$, $M_2CO_3$ or MOH, M+ is for example $NH_4{}^+$ or a metal such as Li+, Na+ or K+.

The hydroxycarbonylphosphonic acid triesters may be prepared by methods analogous to those described above in A–J and S.

V. Reacting hydroxycarbonylphosphonic acid with an esterifying halide, using a tetraalkylammonium salt as a catalyst, according to the formula

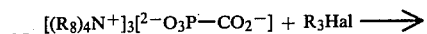

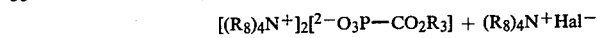

Hal is Cl, Br or I. $R_3$ has the meaning given above and $R_8$ is an alkyl residue, such as for example n-butyl, n-pentyl, n-hexyl, n-heptyl and n-octyl. Preferably n-heptyl is used and preferably the reaction is performed as an extractive alkylation, as described by for example A. Brändström, Preparative Ion Pair Extraction (Apotekarsocieteten, Hässle; Sweden 1976).

Also as described, the phosphonate groups may be transformed to a disalt

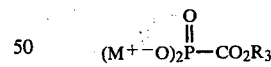

where M+ is for example $NH_4{}^+$ or a metal such as Li+, Na+ or K+.

W. Reacting oxycarbonylphosphonic acid diesters according to the formula:

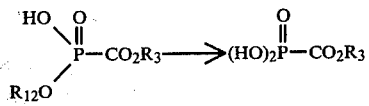

$R_3$ and $R_{12}$ have the meaning described above.

The preparations may be performed by procedures analogous to those described above in S–U.

Optionally the oxycarbonylphosphonic acid monocarboxylic ester thus obtained may be neutralized with a weak cation exchanger or with a base such as MHCO₃, M₂CO₃ or MOH. M⁺ is for example $NH_4^+$ or a metal such as $Li^+$, $Na^+$ or $K^+$.

The oxycarbonylphosphonic acid diesters may be prepared by methods described above in O-R.

Preparation of triesters of hydroxycarbonylphosphonic acid.

Example 1. Hydoxycarbonylphosphonic acid triphenyl ester 7.87 g (0.03 mole) of ethyl diphenylphosphite (B. F. Griffin and A. Burger, J. Amer. Chem. Soc. 78 (1956) 2336) and 9.39 g (0.06 mole) of freshly distilled phenyl chloroformate were heated at 110° overnight. Volatile components were evaporated in vacuo to give 10,5 g (98%) of the title compound as a residue. Analysis by gas liquid chromatography (Perkin-Elmer column OV 17, 250° C.) shows a practically pure compound (>95%). NMR (CDCl₃)δ: 6,90–7,33 (multiplet).

Example 2. Di-p-tolyl phenoxycarbonylphosphonate 29,0 g (0,1 mole) of ethyl di-p-tolylphosphite and 31,3 g (0.2 mole) of phenyl chloroformate were heated at 110° overnight. Volatile components were evaporated in vacuo (0,3 mm) at 110° to give the title compound as a residue. $n_D^{25}$ 1.5554 NMR (CDCl₃)δ: 2,30 (S, CH₃) 6,9–7,6 (m, aryl). IR (neat)cm⁻¹: 1740 (CO), 1590, 1510, 1300, 1190, 1160, 970.

An example of methods used for the synthesis of triesters of phosphorous acid.

Example 3. Ethyl di-p-tolylphosphite

The synthesis was carried out by the method described by B. S. Griffin and A. Burger JACS 78 (1956) 2336 for the preparation of ethyl diphenylphosphite. A solution of 103.85 g (0.37 mole) di-p-tolyl phosphorochloridite in 175 ml of dry hexane was added with stirring and over a period of four hours to an ice-cold solution of 29.27 g (0.37 mole) of pyridine and 18.00 g (0.39 mole) of absolute ethanol in 175 ml of dry hexane. The mixture was stirred at room temperature overnight. The pyridinium chloride was filtered off and was washed with dry hexane. The solvent was removed in vacuo (15 mm) on a rotavapor. The residual oil was fractionated by distillation in vacuo. The fraction boiling at 138°–165° C. 0.03 mm was collected to yield 74.5 g of a colourless oil (69%). $n_D^{25}$ 1.5382. Analysis for C₁₆H₁₉O₃P. Found (Calculated): C 65.61 (66.20), H 6.48 (6.20), P 10.47 (10.67). NMR (CDCl₃)δ: 1.27 (t,J 7 Hz, CH₃), 2.20 (s, Ar-CH₃), 4.20 (quintet, J 7 Hz, CH₂), 7.02 (s, aryl). IR (neat) cm⁻¹: 2980, 1610, 1510, 1200, 1170, 1030, 950.

Preparation of diesters of hydroxycarbonylphosphonic acid.

Example 4. Sodium phenyl phenoxycarbonylphosphonate 10.7 g (0.03 mole) or hydroxycarbonylphosphonic acid triphenyl ester and 50 g (wet weight, 0.09 mole) of Amberlite IRC 50 (Na⁺) were stirred in 100 ml of water, at room temperature overnight. Ethanol was added and the solution was filtered and evaporated in vacuo. The residue was redissolved in 25 ml of hot ethanol, filtered and precipitated by the addition of 300 ml of ether. The precipitate (5.11 g) was recrystallized twice from i-propanol to give 3.20 g (35%) of the title compound.

Analysis for C₁₃H₁₀NaO₅P. Found (calculated): Na 7.8 (7.7). Molecular weight by titration: 305.1 (300.2).

Example 5. Sodium phenyl phenoxycarbonylphosphonate 3.54 g (10 mmole) of hydroxycarbonylphosphonic acid triphenyl ester and 0.80 g (9.5 mmole) of sodium hydrogen carbonate in 10 ml of water were stirred at room temperature overnight. The solvent was evaporated in vacuo, the residue was extracted with 50 ml of ethanol and the ethanol solution was filtered and evaporated. Yield 2.20 g. T.l.c. (silica gel, etanol) R_f 0.74. Analysis for C₁₃H₁₀NaO₅P. Found (calculated): 8.2 (7.7). The compound was recrystallized twice i-propanol to give 0.31 g (10%) of the title compound. T.l.c. (silica gel, etanol): R_f 0.73 (single spot). By t.l.c. (polyethyleneimine, 1 M LiCl, molybdate spray) the compound was shown to contain <0.5% of trisodium oxycarbonylphosphonate.

Analysis for C₁₃H₁₀NaO₅P. Found (calculated): Na 7.9 (7.7). Molecular weight by titration: 297(300.2).

Example 6. Similar to the description in example 5, sodium p-tolyl phenoxycarbonylphosphonate was also obtained From di-p-tolyl phenoxycarbonylphosphonate yield 26%. T.l.c. (silica gel, ethanol): R_f 0.61 single spot. By t.l.c. (polyethyleneimine, 1 M LiCl, molybdate spray) the compound was shown to contain <0.4% of trisodium oxycarbonylphosphonate. C₁₄H₁₂NaO₅P: Found (calculated): C 52.42 (53.52), H 3.95 (3.85), Na 7.38 (7.32). P 10.10 (9.86).

Example 7. Sodium p-methoxyphenyl phenoxycarbonylphosphonate 13.7 g (41 mmole) of ethyl p-methoxyphenyl phenoxycarbonylphosphonate and 12.5 g (82 mmole) of bromotrimethylsilane were stirred under an atmosphere of argon at room temperature overnight. Volatile components were evaporated in vacuo (0.3 mm). The residue was added dropwise over a period of 10 min, to a cation exchanger, (IRC Na⁺, 68 g wet, 120° mekv) in 150 ml of water. The mixture was stirred overnight. The ion exchanger was filtered off and was washed with water and ethanol. The solvent was evaporated in vacuo and the residue was mixed with 100 ml of water and was extracted with 2×50 ml of ether. The water phase was evaporated at reduced pressure (0.3 mm). The residue was treated with 250 ml of absolute boiling ethanol and the mixture was filtered while still hot. 1.30 g of crystalline material was filtered off. The ethanol was evaporated and the residue was dissolved in 50 ml of absolute ethanol. Dry ether was added to precipitate crude sodium p-methoxyphenyl phenoxycarbonylphosphonate 8.82 g, which was recrystallized from i-propanol to give 5.44 g. It was further purified on a column of silica gel eluted with ethanol and finally recrystallized twice from i-propanol to give 3.65 g (27%) of sodium p-methoxyphenyl phenoxycarbonylphosphonate. Analysis for C₁₄H₁₂NaO₆P. Found (calculated): Na 7.2 (7.0). Molecular weight by titration 323 (330). T.l.c. (silica gel, ethanol, sprayed consecutively with molybdate and aqueous SnCl₂ with drying inbetween): R_f 0.51 single spot. By t.l.c. (polyethyleneimine, 1 M LiCl, molybdate spray) the compound was estimated to contain <0.2% of trisodium oxycarbonylphosphonate. IR (KBr)cm⁻¹: 1710 (CO), 1510, 1270, 1090 910.

Example 8. Similar to the description in example 7, sodium p-chlorophenyl phenoxycarbonylphosphonate was prepared and analyzed From ethyl p-chlorophenyl phenoxycarbonylphosphonate. Yield 36%. T.l.c. $R_f$ 0.54 single spot. By t.l.c. the compound was estimated to contain <0.2% of trisodium oxycarbonylphosphonate. IR(KBr) cm$^{-1}$: 1710 (CO), 1490, 1270, 1090, 910. Preparation of monoesters of hydroxycarbonylphosphonic acid (of the phosphonic acid group).

Example 9. Phenyl disodium oxycarbonylphosphonate 3.06 g (10 mmole) of diphenyl ethoxycarbonylphosphonate and 19,0 ml of 1.05 N NaOH were heated at reflux for 1 hour. The solution was evaporated in vacuo and the product was redissolved in H$_2$O. The product precipitated with methanol (1.54 g). It was contaminated with some trisodium oxycarbonylphosphonate. It was redissolved in water (10 ml) and ethanol was added until about 1/10 of the total amount had precipitated. This was discarded by filtration. Ethanol was added to the solution and the precipitate was collected and underwent the same selective precipitation procedure once more to give 0.80 g (32%) of phenyl disodium oxycarbonylphosphonate. Analysis for C$_7$H$_5$Na$_2$O$_5$P. Found (calculated): C 33.91 (34.17), H 1.88 (2.05). Na 18.63 (18.68), P 12.63 (12.59). Equivalent weight by titration: 124.4 (123.0). By t.l.c. (polyethyleneimine, 1 M LiCl, molybdate spray) the compound was shown to contain <0.5% of trisodium oxycarbonylphosphonate.

Example 10. Analogous to the description in example 9, p-tolyl disodium oxycarbonylphosphonate was prepared From 11.47 g (30 mmole) di-p-tolyl phenoxycarbonylphosphonate (0° C. 1 hour, room temperature, overnight, nitrogen atmosphere). Yield 6.51 g (83%) T.l.c. (polyethyleneimine, 1 M LiCl, molybdate spray) $R_f$ 0.51 single spot. By t.l.c. the compound was estimated to contain <0.4% of trisodium oxycarbonylphosphonate.

Analysis for C$_8$H$_7$Na$_2$O$_5$P. Found (calculated): C 36.77 (36.94), H 2.71 (2.71), P 11.87 (11.91), Na 17.60 (17.68). NMR (D$_2$O)δ: 4.61 (s, CH$_3$), 6.90–7.28 (C$_6$H$_4$). IR (KBr)cm$^{-1}$: 1610, 1590, 1220, 1080, 910.

Example 11. p-Methoxyphenyl disodium oxycarbonylphosphonate 16.8 g (50 mmole) of ethyl p-methoxyphenyl phenoxycarbonylphosphonate, was stirred under an atmosphere of argon with 12.5 ml (82 mmole) of bromotrimethylsilane for 5 hours. Excess of bromotrimethylsilane was evaporated in vacuo (0.3 mm). The mixture was added dropwise to 100 ml of 1.00 M NaOH (0.10 mole) during 10 minutes. The stirring was continued at room temperature during 4 hours. The mixture was extracted with 3×75 ml of ether. The water phase was evaporated in vacuo and the residue was dissolved in 50 ml of water. The crude disodium p-methoxyphenyl oxycarbonylphosphonate was precipitated with 500 ml of ethanol. Yield 12.1 g. It was contaminated with some trisodium oxycarbonylphosphonate. It was redissolved in water (50 ml) and ethanol (70 ml) was added slowly. The small amount of precipitate was discarded by filtration. Ethanol, 400 ml, was added to the solution and the new precipitate was collected: yield 11.1 g.

Analysis for C$_8$H$_7$Na$_2$O$_6$P. Found (calculated): Na 17.5% 16.65). For further purification it was precipitated with etanol from a water solution two more times. Yield 8.3 g (60%). T.l.c. (polyethyleneimine, 1 M LiCl, molybdate spray): $R_f$ 0.57, single spot. By t.l.c. (the same system) the compound was estimated to contain <0.4% of trisodium oxycarbonylphosphonate. Analysis for C$_8$H$_7$Na$_2$O$_6$P. Found (calculated): C 34.94 (34.80), H 2.55 (2.56), Na 16.82 (16.65), P 11,38 (11,22). IR (KBr)cm$^{-1}$: 1590, 1510, 1240, 1210, 1080, 900.

Example 12. Analogous to the description in example 11, the following compounds were prepared and analysed (a) p-Chlorophenyl disodium oxycarbonylphosphonate From ethyl p-chlorophenyl phenoxycarbonylphosphonate. Yield 64% after the first precipitation from water with ethanol. Further purification by repeated precipitations gave a yield of 32% T.l.c. $R_f$ 0.51, single spot. By t.l.c. the compound was estimated to contain <0.4% of trisodium oxycarbonylphosphonate. IR (KBr)cm$^{-1}$: 1590, 1490, 1240, 1220, 1080, 900.

(b) 2,6-Dimethylphenyl disodium oxycarbonylphosphonate

From ethyl 2,6-dimethylphenyl methoxycarbonylphosphonate. Yield 78%. T.l.c. $R_f$ 0.56, single spot. By t.l.c. the compound was estimated to contain <0.4% of trisodium oxycarbonylphosphonate NMR (D$_2$O)δ: 2.30 (s, CH$_3$) 7.07–7.27 (C$_6$H$_3$). IR (KBr)cm$^{-1}$: 1610 (CO), 1490, 1390, 1230, 1200, 1100, 1080, 930.

(c) 5-Indanyl disodium oxycarbonylphosphonate

From ethyl 5-indanyl methoxycarbonylphosphonate. Yield 72%. T.l.c. $R_f$ 0.39, single spot. By t.l.c. the compounds was estimated to contain <0.4% of tridosium oxycarbonylphosphonate. Analysis for C$_{10}$H$_9$O$_5$P-Na$_2$×H$_2$O. Found (calculated): C 39.29 (39.42), H 3.20 (3.65), Na 16.8 (15.1), H$_2$O 6.4 (5.9). NMR (D$_2$O)δ: 1.8–2.3 (CH$_2$), 2.7–3.0 (CH$_2$-C-CH$_2$), 6.9–7.3 (C$_6$H$_3$) IR (KBr) cm$^{-1}$: 1600 (CO), 1500, 1480, 1250, 1230, 1090, 970.

(d) 4-Acetylphenyl disodium oxycarbonylphosphonate

From 6,0 g (16 mmole) of methyl p-acetylphenyl p-nitrophenoxycarbonylphosphonate and 3.05 g (20 mmole) of bromotrimethylsilane. After the reaction excess of bromotrimethylsilane was evaporated in vacuo and the residue was added to 30 g (about 50 meq) of Amberlite IRC 50 (Na$^+$) in 50 ml of H$_2$O and stirred at room temperature. The solution was filtered, washed with ether and centrifuged. The water solution was treated with activated carbon and filtered. By repeated precipitations from water solutions with ethanol, 4-acetylphenyl disodium oxycarbonylphosphonate was obtained. T.l.c. $R_f$ 0.56. By t.l.c. the compound was estimated to certan 5–10% of trisodium oxycarbonylphosphonate. NMR (D$_2$O)δ: 2.67 (S, CH$_3$), 7.32 and 8.05 (doublets, J 9 Hz, C$_8$H$_4$) IR (KBr) cm$^{-1}$: 1590, 1370, 1240, 1080, 900.

Examples of methods for the preparation of monoesters of the carboxylic group of hydroxycarbonylphosphonic acid.

Example 13. Disodium phenoxycarbonylphosphonate 1.26 g (5.5 mmole) of dimethyl phenoxycarbonylphosphonate and 2.52 g (16.4 mmole) of bromotrimethylsilane were stirred at room temperature overnight in a dried flask. Volatile components were evaporated in vacuo (1 mm) and the residue was stirred with 20 g (36 meq) of Amberlite IRC 50 (Na+) in 15 ml of water for 2 hours. The solution was filtered and the ion exchanger was washed (on a column) with 25 ml of water. The combined water solutions were washed with 3×10 ml ether, filtered and evaporated in vacuo. The residue was washed with ethanol to give 1.24 g (88%) of disodium phenoxycarbonylphosphonate. T.l.c. (polyethyleneimine, 1.4 M LiCl, molybdate spray): $R_f$ 0.43, single spot. By t.l.c. the compound was estimated to contain <0.5% of trisodium oxycarbonylphosphonate. Analysis for $C_7H_5Na_2O_5P \times \frac{3}{8}H_2O$. Found (calculated): $H_2O$ 4.5 (4.6), Na 17.9 (17.8). Molecular weight by titration 269 (258). NMR $(D_2O)\delta$: 7.08–7.54 ;L (m, $C_6H_5$).

Example 14

Similar to the description in example 13, the following compounds were prepared and analysed.

(a) Disodium p-tolyloxycarbonylphosphonate

From dimethyl p-tolyloxycarbonylphosphonate. Yield 87%. T.l.c. (1 M LiCl) $R_f$ 0.65, single spot. By t.l.c. it can be estimated to contain <0.5% of trisodium oxycarbonylphosphonate. Analysis for $C_8H_7Na_2O_5P \times \frac{1}{3}H_2O$. (After drying in vacuo.) Found (calculated): $H_2O$ 2.40 (2.26). C 35.95 (36.10), H 3.09 (2.65), P 11.44 (11.64). NMR $(D_2O)\delta$: 2.35 ($CH_3$), 7.0–7.4 ($C_6H_4$), IR (KBr)cm$^{-1}$: 1720 (CO), 1210, 1170, 1150 and 980.

(b) Disodium p-methoxyphenoxycarbonylphosphonate

From diethyl p-methoxyphenoxycarbonylphosphonate. Yield 85%. T.l.c. (1 M LiCl) $R_f$ 0.45, single spot. By t.l.c. the compound was estimated to contain <0.5% of trisodium oxycarbonylphosphonate. Analysis for $C_8H_7O_6Na_2P \times H_2O$. Found (calculated) C 32.92 (32.67), H 2.67 (3.08), P 10.44 (10.3). NMR $(D_2O)\delta$: 3.80 (s, $CH_3O$), 6.9–7.3 ($C_6H_4$).

(c) Disodium p-chlorophenoxycarbonylphosphonate

From 5.8 g (20 mmole) of diethyl 4-chlorophenoxycarbonylphosphonate and 12.5 g (80 mmole) of bromotrimethylsilane. 5.0 g (89%) of disodium 4-chlorophenoxycarbonylphosphonate was obtained. T.l.c. $R_f$=0.40. Apparently the compound decomposes during thin layer chromatography (1 M LiCl, 3 hours) and a tailing of the single spot can be detected. By t.l.c. the compound can be estimated to cotain 1–2% of trisodium oxycarbonylphosphonate. Another synthesis gave a yield of 4.4 g (78%), after drying in a desiccator. T.l.c. $R_f$ 0.37. By t.l.c. the compound was estimated to contain <1% of trisodium oxycarbonylphosphonate. Tailing of the compound obscured any lower detection limit. Analysis for $C_7H_4ClNa_2O_5P$. Found (calculated): C 29.15 (29.97), H 1.73 (1.44), P 11.13 (11.04). NMR $(D_2O)\delta$: 7.1–7.6 ($C_6H_4$).

(d) Disodium 3,4-dichlorophenoxycarbonylphosphonate

From 5.0 g (17 mmole) of dimethyl 3,4-dichlorophenoxycarbonylphosphonate. By t.l.c. the crude product (4.8 g) was estimated to contain <1% of trisodium oxycarbonylphosphonate and approximately 5% inorganic phosphate ($PO_4^{3-}$). This crude product was used for the first biological tests. The crude product (2.8 g) was purified by dissolving in 6.5 ml of distilled $H_2O$ and 13 ml of ethanol was slowly added. The precipitate was filtered off, and about 150 ml of ethanol was added to the solution to give a new precipitate. This precipitate was collected and passed through one more precipitation cycle to give purified disodium 3,4-dichlorophenoxycarbonylphosphonate. T.l.c. $R_f$=0.33, single spot. Apparently the product slowly decomposes during thin layer chromatography (1 M LiCl, 3 hours) and a very weak tailing of the single spot can be detected. By t.l.c. the compound can be estimated to contain <1% of trisodium oxycarbonylphosphonate. Analysis for $C_7H_3Cl_2Na_2O_5P \times \frac{1}{2}H_2O$ (After drying in vacuo). Found (calculated): $H_2O$ 2.69 (2.78) C 25.83 (25.95), H 1.18 (0.93), P 9.40 (9.56). NMR $(D_2O)\delta$: 7.3–7.7 ($C_6H_3$). IR (KBr)cm$^{-1}$: 1710 (CO) 1150 and 990 ($PO_4^{3-}$).

(e) Disodium p-(ethoxycarbonyl)phenoxycarbonylphosphonate

From 6.6 g (20 mmole) of diethyl p-(ethoxycarbonyl)phenoxycarbonylphosphonate. The crude product (5.4 g) was purified by precipitation from water: 5.1 g was dissolved in 10 ml of water and filtered. 20 ml of ethanol was added and the precipitate was filtered. Another 200 ml of ethanol was added to the filtrate and the new precipitate was collected, washed with ethanol and ether and dried in vacuo. Yield 1.4 g (22%). T.l.c. (1 M LiCl) $R_f$ 0.47. By t.l.c. the compound was estimated to contain <0.4% of trisodium oxycarbonylphosphonate. NMR $(D_2O)\delta$: 1.37 (t, J 7 Hz, $CH_3$), 4.35 (q, J 7 Hz, CH), 7.35 and 8.02 (doublets, J 9 Hz).

Triesters of hydroxycarbonylphosphonic acid used as starting materials for the synthesis of the various di- and mono esters of the same acid, may be prepared by known methods as described in A-J and S above. Below follows, in addition to the examples 1 and 2 already given, further examples of such syntheses.

Example 15

Analogous to the descriptions in examples 1 and 2 the following compounds were prepared by heating the phosphite triester and the chloroformate ester at a temperature from 20° to 130° for 1 to 15 hours.

(a) Ethyl p-methoxyphenyl phenoxycarbonylphosphonate

From 24.4 g (0.10 mole) of diethyl p-methoxyphenylphosphite and 31.2 g (0.20 mole) of phenyl chloroformate (130°, 2 hours). $n_C^{25}$ 1.5378 NMR $(CDCl_3)\delta$: 1.42 (t, J 7 Hz, $CH_3$-C), 3.80 (s, $CH_3O$) 4.50 (quintet, J 7 Hz, $CH_2$) 6.76–7.70 (9H). IR (neat) cm$^{-1}$: 1740, 1590, 1500, 1180, 980 and 920.

(b) Ethyl, p-chlorophenyl phenoxycarbonylphosphonate

From 24.9 g (0.10 mole) of diethyl p-chlorophenylphosphite and 31.3 g (0.20 mole) of phenyl chloroformate (110°, about 15 hours) NMR $(CDCl_3)\delta$: 1.47 (t, J 7 Hz, $CH_3$-C), 4.50 (quintet, J 7 Hz, $CH_2$), 7.0–7.7 (aromatic).

(c) Ethyl 2,6-dimethylphenyl methoxycarbonylphosphonate

From 20.0 g (83 mmole) of diethyl 2,6-dimethylphenylphosphite and 10.0 ml (127 mmole) of methyl chloroformate (100°, 4 hours). Yield 22.2 g (99%). By g.l.c. (3% OV 17 column, 120°–280°) only one peak was seen. NMR $(CDCl_3)\delta$: 1.35 (t, J 7 Hz, $CH_3$-C), 2.37 (s, $CH_3$-Ar), 3.92 (s, $CO_2CH_3$), 4.40 (quintet, J 7 Hz, $CH_2$), 7.03 (s, $C_6H_3$). An analytical sample was distilled in vacuo B.p.$_{0.04}$ 125°–8°. $n_D^{25}$ 1.4914.

(d) Ethyl, 5-indanyl methoxycarbonylphosphonate

From 20,0 g (78 mmole) of diethyl 5-indanylphosphite and 10.0 ml (127 mmole) of methyl chloroformate (100°, 4 hours). yield 22 g (99%). By g.l.c. (3% OV17 column, 120°–280°) the purity was estimated to be about 85%. NMR $(CDCl_3)\delta$: 1.40 (t, J 7 Hz, $CH_3$-C) 1.85–2.35

(multiplet, $CH_2$), 2.80–3.05 ($CH_2$-C-$CH_2$), 3.82 (s, $CO_2CH_3$), 4.42 (quintet, J 7 Hz, $CH_2O$), 6.9–7.3 ($C_6H_3$).

(e) Methyl p-acetylphenyl p-nitrophenoxycarbonylphosphonate

From 3.78 g (17 mmole) of dimethyl p-acetylphenylphosphite and 3.34 g (17 mmole) of p-nitrophenyl chloroformate (freshly recrystallized from n-hexane) (Room temperature, 4 hours). NMR ($CDCl_3$)δ: 2.63 (s, $CH_3CO$), 4.20 (d, J 12 Hz, $CH_3O$), 7.5–7.6 and 8.0–8.5 ($C_6H_4 + C_6H_4$).

Example 16. Diethyl 4-methoxyphenoxycarbonylphosphate 18.6 g (0.12 mole) of triethylphosphite was heated at 125°–130° in a flask with a reflux condenser. 18.6 g (0.10 mole) of 4-methoxyphenyl chloroformate (prepared according to M. J. Zabik and R. D. Schuetz, J. Org. Chem. 32 (1967) 300) was added dropwise. The reaction flask was heated additionally at about 120° for 1½ hours and left at room temperature overnight. The product was distilled to give 25.8 g (89%) of diethyl 4-methoxyphenoxycarbonylphosphonate. B.p.$_{0.03}$ 174°–8°, $n_D^{21}$ 1.4940. Analysis for $C_{12}H_{17}O_6P$. Found (calculated): C 49.79 (50.00), H 6.01 (5.95), P 10.54 (10.75). NMR ($CDCl_3$)δ: 1.42 (t, $CH_3$), 3.78 (s, $OCH_3$), 4.13–4.63 ($CH_2$), 6.77–7.33 (aromatic). IR (neat) cm$^{-1}$: 1740 (CO), 1275, 1255, 1190, 1030.

Example 17

Analogous to the description in example 16, the following compounds were prepared by heating the phosphite triester and the chloroformate ester at 80° to 130° for 1 to 10 hours.

(a) Dimethyl phenoxycarbonylphosphonate

From 10.0 ml (85 mmole) of trimethylphosphite and 10.0 g (64 mmole) of phenylchloroformate (100°, 2 hours). Yield 11.0 g (75%). B.p.$_{0.5}$ 125°–7°, $n_D^{25}$ 1.4907. NMR ($CDCl_3$)δ: 3.90 and 4.09 ($CH_3$), 7.10–7.60 ($C_6H_5$).

(b) Dimethyl p-tolyloxycarbonylphosphonate

From 10.3 g (85 mmole) of trimethylphosphite and 10.3 g (60 mmole) of p-tolyl chloroformate (prepared according to M. J. Zabik and R. D. Scheutz J. Org. Chem. 32 (1967) 300). (100°, 2 hours) yield 93%. B.p.$_{0.2}$ 131°, $n_D^{20}$ 1.4972. Analysis for $C_{10}H_{13}O_5P$. Found (calculated): C 49.37 (49.18). H 5.53 (5.36), P 11.71 (12.69). NMR ($CDCl_3$)δ: 2.40 ($CH_3$), 3.92 and 4.12 ($CH_3O$), 6.97–7.37 (aromatic protons).

A second distillation gave a yield of about 80%. New analysis: C 49.13 (49.18), H 5.41 (5.36), P 12.71 (12.69).

(c) Diethyl 4-chlorophenoxycarbonylphosphonate

From 20 g (0.12 mole) of triethylphosphite and 19.1 g (0.10 mole) of 4-chlorophenyl chloroformate (prepared according to M. J. Zabik and R. D. Scheutz J. Org. Chem. 32 (1967) 300). (125°, 2 hours) yield 26.3 g (90%). B.P.$_{0.01}$ 153°–6°, $n_D^{21}$ 1.4980. Analysis for $C_{11}H_{14}ClO_5P$. Found (calculated): C 44.85 (45.14), H 4.83 (4.82), P 10.54 (10.59). NMR ($CDCl_3$)δ: 1.45 (t, $CH_3$), 4.17–4.63 ($CH_2$), 7.03–7.48 ($C_6H_4$).

(d) Dimethyl 3,4-dichlorophenoxycarbonylphosphonate

From 10.3 g (85 mmole) of trimethylphosphite and 13.5 g (60 mmole) of 3,4-dichlorophenyl chloroformate (100°, 2 hours). Yield 11.4 g (64%) B.p.$_{0.04}$ 164° C. $n_D^{20}$ 1.5271. Solidifies to colourless crystals m.p. 58°–9° C.

Analysis for $C_9H_9Cl_2O_5P$. Found (calculated): C 36.06 (36.14), H 3.31 (3.03), Cl 23.58 (23.71), P 10.50 (10.36). NMR ($CDCl_3$)δ: 3.93 and 4.07 ($CH_3O$), 7.0–7.6 ($C_6H_3$) IR (KBr)cm$^{-1}$: 1740 (CO), 1265, 1200, 1165, 1055, 1020.

(e) Diethyl 4-(ethoxycarbonyl)phenoxycarbonylphosphonate

From 21.6 g (0.13 mole) of triethylphosphite and 22.8 g (0.10 mole) of 4-ethoxycarbonylphenyl chloroformate (120°, 2 hours). Yield 26.0 g (87%) Bp$_{0.01}$ 190°–2°. $n_D^{25}$ 1,4890.

Analysis for $L_{12}H_{15}O_7P$. Found (calculated): C 50.77 (50.91), H 6.20 (5.80), P 9.53 (9.38).

(f) Diphenyl ethoxycarbonylphosphonate

[According to A. Takamizawa and Y. Sato, Chem. Pharm. Bull. 12 (1964) 398] Yield 97% B.p.$_{0.03}$ 153°–5°, $n_D^{25}$ 1.5314.

Examples of methods, used for the synthesis of haloformate esters.

Example 18. 3,4-dichlorophenyl chloroformate 40.75 g (0.25 mole) of 3,4-dichlorophenol in 135 ml of dry toluene was cautiously added to 240 ml (0.46 moles) of a 20% solution of phosgene in toluene. The reaction flask was equipped with a stirrer, a dry ice condensor and a dropping funnel, and the reaction temperature was 20°–25°. 31.5 g (0.26 moles) of N,N-dimethylaniline was added over a period of 45 minutes and the flask was left without stirring for 2 hours. The precipitate was filtered off and washed with 2×25 ml of toluene. The combined toluene solutions were cooled on ice and quickly washed with 50 ml of water, 100 ml of 0.1 N HCl and 100 ml of water. The solution was dried over magnesium sulfate and evaporated on a rotary evaporator. The residue was distilled in vacuo over a Vigreux column, to give 46.4 g (62%) of 3,4-dichlorophenylchloroformate, bp$_{20}$ 134°. The product becomes slightly blue and crystallizes in long needles, mp 51°–53° C.

Example 19. 4-Ethoxycarbonylphenyl chloroformate

From 49.9 g (0.3 mole) of 4-hydroxybenzoic acid ethyl ester, 40 ml (0.3 mole) of N,N-dimethylaniline and 0.4 mole of a 20% solution of phosgene in toluene, 54.4 g (79%) of 4-ethoxycarbonylphenyl chloroformate was obtained. Bp 146°–146.5°, $n_D^{25}$ 1.5140. IR (neat)cm$^{-1}$: 1720 and 1790 (CO).

Further examples of the synthesis of triesters of phosphorous acid, used as starting materials in the preparations of triesters of hydroxycarbonylphosphonic acid, described above.

Example 20. Diethyl p-methoxyphenylphosphite

The synthesis was carried out by the method described by W. G. Bentrude, E. R. Hansen, W. A. Khan, T. B. Min and P. E. Rogers J. Amer. Chem. Soc. 95 2292 (1973) for the preparation of diethyl phenylphosphite.

A solution of 50.0 g (0.364 mole) of phosphorous trichloride in 500 ml of anhydryous ether was stirred (mechanically) under an atmosphere of argon. The temperature was maintained at −20°–15° C. during the addition of 37.1 g triethylamine, followed by the slow addition of p-methoxyphenol, 45.19 g (0.364 mole) in 200 ml of dry ether over a period of 2,5 hours. When the addition was complete another portion of triethylamine 73.8 g (0.728 mole), was added. followed by the slow addition of absolute ethanol, 33.5 g (0.728 mole), in 50 ml of dry ether (1.5 hours). The mixture was stirred at room temperature over night. The mixture was warmed and allowed to reflux for 1 hour. The triethylamine hydrochloride was filtered off and was washed with dry ether. The solvent was removed under reduced pressure. Distillation of the residual oil yielded 48.6 g of diethyl p-methoxyphenylphosphite, bp 110 (1.2 mm)-102 (0.6 mm). Another 4.20 g was obtained at 0.2 mm bp 92°–96° C. $n_D^{20}$ 1.4993. Analysis for $C_{11}H_{17}O_4P$. Found (calculated): C 54.14 (54.10), H 7.07 (7.02), P 12,74 (12,68). NMR (CDCl$_3$)δ: 1.26 (t, J 7 Hz, CH$_3$), 3.70 (s, CH$_3$O), 4.00 (quintet, J 7 Hz, CH$_2$), 6.7–7.1 (m, C$_6$H$_4$). IR (neat) cm$^{-1}$: 2980, 1510, 1220, 1030, 920.

Example 21.

Analogously as described in example 20, the following phosphites were prepared.

(a) Diethyl p-chlorophenylphosphite

Yield 43%. Bp$_{1.5}$ 102°–104° C., $n_D^{25}$ 1.5047. NMR (CDCl$_3$)δ: 1.17 (t, J 7 Hz, CH$_3$), 4.00 (quintet, J 7 Hz, CH$_2$), 6.9–7.3 (C$_6$H$_4$). IR (neat)cm$^{-1}$: 2980, 1590, 1490, 1390, 1030, 920.

(b) Diethyl 2,6-dimethylphenylphosphite

Yield 29%. Bp$_{0.01}$ 84°–5°, $n_D^{25}$ 1.4951. NMR (CDCl$_3$)δ: 1.30 (t, J 7 Hz, CH$_3$-C), 2.33 (s, CH$_3$-Ar), 4.03 (quintet, J 7 Hz, CH$_2$O), 7.00 (s, C$_6$H$_3$).

(c) Diethyl 5-indanylphosphite

Yield 29%. Bp$_{0.01}$ 140°, $n_D^{25}$ 1.5102. NMR (CDCl$_3$)δ: 1.30 (t, J 7 Hz, CH$_3$), 1.95–2.30 (CH$_2$), 2.97–3.03 (CH$_2$-C-CH$_2$), 4,03 (quintet, J 7 Hz, CH$_2$O), 6.7–7.3 (C$_6$H$_3$).

(d) Dimethyl p-acetylphenylphosphite

Yield 20%. Bp$_{0.03}$ 128°–130°, $n_D^{25}$ 1.5308. Analysis for $C_{10}H_{13}O_4P$. Found (calculated): C 52.36 (52.64), H 5.74 (5.74), P 13.33 (13.37). NMR (CDCl$_3$)δ: 2.58 (s, CH$_3$O), 3.68 (d, J 11 Hz, CH$_3$O), 7.14 and 7.98 (d, J 9 Hz).

Pharmaceutical compositions

The following examples illustrate the preparation of pharmaceutical compositions of the invention. The active substance in case it can form salts, is preferably used in the form of its sodium salt.

Example 22. Aerosol for inhalation

| Active substance | 1.00 g |
|---|---|
| Miglyol ® | 0.20 g |
| Frigen ® 11/12/113/114 | ad 100.0 g |

Example 23. Tablets

| Each tablet contains: | |
|---|---|
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

Example 24. Suppositories

| Each suppository contains: | |
|---|---|
| Active substance | 20.0 mg |
| Ascorbyl palmitate | 1.0 mg |
| Suppository base (Imhausen H or Witespol ® H) | ad 2000.0 mg |

Example 25. Syrup

| Active substance (as its sodium salt) | 0.200 g |
|---|---|
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 g |

Example 26. Injection solution

| Active substance (as its sodium salt) | 0.500 mg |
|---|---|
| Sodium pyrosulfite | 0.500 mg |
| Disodium edetate | 0.100 mg |
| Sodium chloride | 8.500 mg |
| Sterile water for injection | ad 1.00 ml |

Example 27. Inhalation solution

| Active substance | 5.00 g |
|---|---|
| Sodium pyrosulfite | 0.10 g |
| Disodium edetate | 0.10 g |
| Sodium chloride | 0.85 g |
| Purified water | ad 100.0 ml |

Example 28. Sublingual tablets

| Active substance | 5.0 mg |
|---|---|
| Lactose | 85.0 mg |
| Talc | 5.0 mg |
| Agar | 5.0 mg |
| | 100.0 mg |

Example 29. Drops

| Active substance | 2.00 g |
|---|---|
| Ascorbic acid | 1.00 g |
| Sodium pyrosulfite | 0.10 g |
| Disodium edetate | 0.10 g |
| Liquid glucose | 50.00 g |
| Absolute alcohol | 10.00 g |
| Purified water | ad 100.0 ml |

Example 30. Syrup

| Active substance (as sodium salt) | 0.200 g |
|---|---|
| Liquid glucose | 30.0 g |
| Sucrose | 50.0 g |
| Ascorbic acid | 0.1 g |
| Disodium edetate | 0.01 g |
| Orange essence with solubilizer | 0.25 g |
| Hydrochloric acid to pH 6.0–8.0 | |
| Purified water | ad 100.0 g |

Example 31. Solution for injection

| Active substance | 0.500 mg |
|---|---|
| Disodium edetate | 0.100 mg |
| Sodium chloride for isotonia q.s. | |
| Hydrochloric acid to pH 6.5–8.0 | |

Example 32. Solution for inhalation

| | |
|---|---|
| Active substance (as its sodium salt) | 5.00 g |
| Disodium edetate | 0.10 g |
| Sodium chloride | 0.85 g |
| Hydrochloric acid to pH 6.0–8.0 | |
| Purified water | ad 100.0 ml |

Example 33. Drops

| | |
|---|---|
| Active substance (as its sodium salt) | 2.00 g |
| Citric acid | 1.00 g |
| Disodium edetate | 0.10 g |
| Liquid glucose | 50.00 g |
| Ethanol 95% | 10.00 g |
| Sodium hydroxide and hydrochloric acid to pH 6.2–6.8 | |
| Purified water | ad 100.0 ml |

Example 34. Solution for topical use

| | |
|---|---|
| Active substance (as its sodium salt) | 2.00 g |
| Isopropanol | 38.0 g |
| Glycerol | 13.6 g |
| Hydrochloric acid to pH 5.0–8.5 | |
| Purified water | ad 100.0 g |

Preparations containing 0.2, 0.5 and 1.0 g of active substance.

Example 35. Jelly

| | |
|---|---|
| Active substance (as its sodium salt) | 4.0 g |
| Methocel ® | 4.0 g |
| Methyl paraoxybenzoate | 0.12 g |
| Propyl paraoxybenzoate | 0.05 g |
| Sodium hydroxide and hydrochloric acid to pH 6.8–8.5 | |
| Distilled water | ad 100.0 ml |

Example 36. Ointment I

| | |
|---|---|
| Active substance (as its sodium salt) | 2.5 g |
| Cetyltrimethylammonium bromide | 0.6 g |
| Stearyl alcohol | 2.25 g |
| Cetanol | 6.75 g |
| Liquid paraffine | 17.0 g |
| Glycerol | 12.0 g |
| Hydrochloric acid to pH 6.0–8.5 | |
| Distilled water | ad 100.0 g |

Preparations containing 0.2, 0.5, 1.0 and 2.0 g of active substance have also been prepared.

Example 37. Ointment II

| | |
|---|---|
| Active substance (as its sodium salt) | 2.5 g |
| Polyethylene glycol 1500 | 50.0 g |
| Polyethylene glycol 4000 | 15.0 g |
| Propylene glycol | ad 100.0 g |

Example 38. Ointment III

| | |
|---|---|
| Active substance (as its sodium salt) | 3.0 g |
| Sorbitan monoleate | 5.0 g |
| Petrolatum | ad 100.0 g |

Example 39. Gastric juice-resistant tablets

Tablets according to Example 4 are coated with an enteric coating solution with the following composition:

| | |
|---|---|
| Cellulose acetate phtalate | 120.0 g |
| Propylene glycol | 30.0 g |
| Sorbitan monoleate | 10.0 g |
| Ethanol 95% | 450.0 ml |
| Acetone | q.s. ad 1000.0 ml |

The coating is carried out by a pouring procedure in a conventional coating pan or by spraying the tablets in a pan spray tablet coater.

Example 40. Eye drops

| | |
|---|---|
| Active substance (as sodium salt) | 0.1 g |
| Disodium edetate | 0.10 g |
| Sodium chloride for isotonia q.s. | |
| Hydrochloric acid to pH 6.5–8.0 | |
| Methocel ® 65 HG 4000 | 0.65 |
| Sterile water | ad 100 ml |

Example 41. Eye drops

| | |
|---|---|
| Active substance (as sodium salt) | 1.0 g |
| Disodium edetate | 0.10 g |
| Sodium chloride for isotonia q.s. | |
| Hydrochloric acid to pH 6.5–8.0 | |
| Methocel ® 65 HG 4000 | 0.65 |
| Sterile water | ad 100 ml |

Example 42. Eye Ointment

| | |
|---|---|
| Active substance (as its sodium salt) | 5 g |
| Paraffin oil | 19 g |
| Petrolatum | 76 g |

Example 43. Cream

| | |
|---|---|
| Active substance | 3.0 g |
| Arlaton ® | 4.0 g |
| Cetanol | 2.0 g |
| Stearic acid | 2.0 g |
| Paraffin oil | 2.0 g |
| Propylene glycol | 2.0 g |
| Glycerol | 1.5 g |
| Methyl-p-hydroxybensoate | 0.06 g |
| Propyl-p-hydroxybensoate | 0.03 g |
| Sodium hydroxide | 0.002 g |
| Hydrochloric acid 2 M to pH 8.0 (water phase) | |
| Distilled water | ad 100 g |

Example 44. Jelly

| | |
|---|---|
| Active substance | 3.0 g |

| -continued | |
|---|---|
| Methocel ® | 2.45 g |
| Glycerol | 10.0 g |
| Tween ® | 0.10 g |
| Methyl-p-hydroxybensoate | 0.06 g |
| Propyl-p-hydroxybensoate | 0.03 g |
| Sodiumhydoxid | 0.002 g |
| Hydrochloric acid 2 M to pH 8.0 | |
| Distilled water | add 100 g |

Biological tests

I. Inhibition of virus multiplication in cell culture
A. Inhibition of herpes simplex type 1 plaque The plaque reduction assay for herpes simplex type 1 was performed on GMK (Green Monkey Kidney) cells as described by Ejereito et al. J. Gen. Virol. 2 (1968) 357. Monolayers on 5 cm petri dishes were used and after virus adsorption the test compound was added in the medium. The results are shown below.

I. Inhibition of virus multiplication in cell culture
A. Inhibition of herpes simplex type 1 plaque The plaque reduction assay for herpes simplex type 1 was performed on GMK (Green Monkey Kidney) cells as described by Ejereito et al. J. Gen. Virol 2 (1968) 357. Monolayers on 5 cm petri dishes were used and after virus adsorption the test compound was added in the medium. The results are shown below.

Inhibition of herpes simplex type 1 plaque on GMK monolayers

| Test compound $R_1-O, O, O$ $\phantom{R_1-O,}P-C-OR_3$ $R_2-O$ | | | | | |
|---|---|---|---|---|---|
| $R_1$ | $R_2$ | $R_3$ | Code | Concentration of test compound (μM) | Inhibition (%) |
|  |  |  | VIS 040<br>VIS 040 | 500<br>100<br>200 | >99.9<br><br>50% |
| Na | 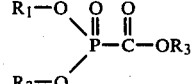 |  | VIS 043<br>VIS 043 | 500<br>100<br>40<br>20 | >99.9<br>>99.9; >99<br>>90.9<br>~80% |
| Na |  | 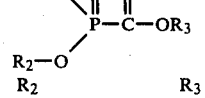 | VIS 058<br>VIS 058 | 500<br>100<br>40<br>10 | >99.9; >99.9<br>88<br>>90<br>~50 |
| Na |  |  | VIS 063<br>VIS 063<br>VIS 063 | 500<br>100<br>20<br>10<br>5 | >99.9; >99.9<br>>99.9<br>69<br>>90<br>~50 |
| Na | 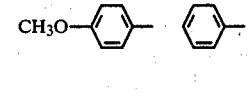 | Na | VIS 041<br>VIS 041 | 500<br>100<br>40<br>10 | >99.9<br>>99.9; 99<br>>90<br>~50 |
|  |  |  | VIS 056<br>VIS 056 | 500<br>100 | >99<br>>99 |
| Na | Na |  | VIS 135 | 100 | 85% |
| Na |  | Na | VIS 059<br>VIS 059<br>VIS 059<br>VIS 059 | 500<br>100<br>20<br>5<br>5 | >99.9; >99.9<br>>99.9<br>95<br>57<br>>90 |
| Na | 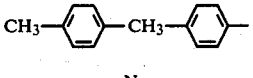 | Na | VIS 067<br>VIS 067<br>VIS 067<br>VIS 067 | 500<br>100<br>20<br>5 | >99.9; >99.9<br>99<br>87<br>57 |
| Na | 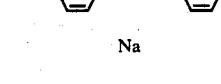 | Na | VIS 066<br>VIS 066<br>VIS 066<br>VIS 066 | 500<br>100<br>20<br>5<br>10<br>5 | >99.9; >99.9<br>>99.9<br>98<br>89<br>>90<br>~75 |
| Na | 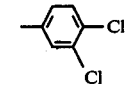 | Na | VIS 442 | 500<br>10 | >99.9<br>>90 |

-continued

| | Test compound $R_1-O, O, O$ $P-C-OR_3$ $R_2-O$ | | | | |
|---|---|---|---|---|---|
| $R_1$ | $R_2$ | $R_3$ | Code | Concentration of test compound (μM) | Inhibition (%) |
| Na | Na |  | VIS 412 VIS 412 | 500 100 100 60 | 80; 88 32; 56 >90 ~50 |
| Na | Na | 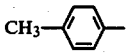 CH$_3$— | VIS 130 | 500 400 200 | 76; 40; 90 >90 ~80 |
| Na | Na | 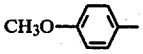 CH$_3$O— | VIS 239 | 500 400 600 | 60; 36; 52; 70 ~60 >90 |
| Na | Na | 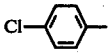 Cl— | VIS 238 VIS 238 | 500 100 100 | 96; 99 52 ~90 |
| Na | | 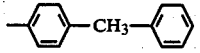—CH$_3$—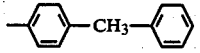 | VIS 065 | 20 10 | >90 ~50 |

B. Inhibition of influenza (WSN Wilson Smith Neurotropic type A.) plaque

The method for plaque assay of influenza has been described by Bentley et al., Archiv für die Gesamte Virusforschung 33 (1971) 234.

Monolayers of MDCK (Madin Darby Canine Kidney) cells on 5 cm plastic petri dishes were inoculated with 100 plaque-forming units of influenza virus (WSN or Victoria). After virus adsorption, 5 ml of agarose overlay containing different concentrations of the test compound were added and the plates were incubated at 34° C. for 4 days. The plaques formed at this time were counted. The results are shown below.

Inhibition of influenza (WSN Wilson Smith Neurotropic type A) plaque on MDCK monolayers.

| | Test compound $R_1-O, O, O$ $P-C-OR_3$ $R_2-O$ | | | | |
|---|---|---|---|---|---|
| $R_1$ | $R_2$ | $R_3$ | Code | Concentration of test compound (μM) | Inhibition (%) |
|  |  |  | VIS 040 VIS 040 | 500 100 | >99 90 |
| Na |  |  | VIS 043 VIS 043 VIS 043 | 500 100 20 | >99.9 84; 90; >99.9 62; 47 |
| Na | CH$_3$O—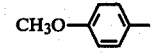 |  | VIS 058 VIS 058 | 500 100 | >99.9 84 |
| Na | Cl—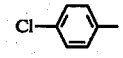 |  | VIS 063 VIS 063 | 500 100 | >99.9 72 |
| Na | 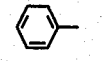 | Na | VIS 041 VIS 041 | 500 20 | >99.9 60; 28 |
| Na | CH$_3$—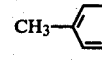 | Na | VIS 059 VIS 059 VIS 059 | 500 100 20 | >99.9; 91; 92 86; 38 58; 36 |
| Na | CH$_3$O—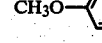 | Na | VIS 067 VIS 067 | 500 100 | 73; >99.9; >99.9 58 |
| Na | Cl—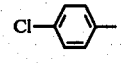 | Na | VIS 066 VIS 066 | 500 100 | >99.9; >99.9 54 |

-continued

| Test compound $R_1O, R_2O \backslash P(=O)-C(=O)-OR_3$ | | | | | |
|---|---|---|---|---|---|
| $R_1$ | $R_2$ | $R_3$ | Code | Concentration of test compound (μM) | Inhibition (%) |
| Na |  | Na | VIS 442 | 500 | 94 |

Inhibition of influenza Victoria plaque on MDCK monolayers:

| $R_1$ | $R_2$ | $R_3$ | Code | Concentration of test compound (μM) | Inhibition (%) |
|---|---|---|---|---|---|
| Na | CH₃—— | — | VIS 065 | 500 / 200 | >99 / 76 |
| CH₃—— | CH₃—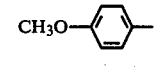— | — | VIS 056 | 200 | 75 |

II. Inhibition of cutaneous herpes on guinea pigs

The effect on cutaneous herpes simplex type 1 infections have been measured in a guinea pig model described by Hubler et al. J. Invest Dermatol 69 (1974) 92. The compounds have been tested as topical applications of 30 μl of 2% solution of the compound in 45% (v/v) isopropanol, 10% (v/v) glycerol and 45% water (v/v) twice daily for 3 days starting 4 hours after infection. The appearance of an infected treated area and a similar infected untreated (only isopropanol-glycerol-water) area was scored daily on a scale from 0 to 3. The total effect is judged from the score at day 5.

| Test compound $R_1O, R_2O \backslash P(=O)-C(=O)-OR_3$ | | | | Score at day 5 | |
|---|---|---|---|---|---|
| $R_1$ | $R_2$ | $R_3$ | Code | treated | untreated |
| Na | Na | phenyl | VIS 412/2 | 0 | 3 |
| Na | CH₃O—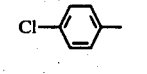— | — | VIS 058 | 2 and 0 respect. in two experiments | 3[x] |
| Na | Cl—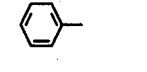— | — | VIS 063 | 2 and 3 respect. in two experiments | 3[x] |
| Na | 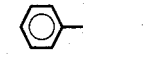— | — | VIS 043[2] | 0 | 3 |
| 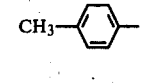— | 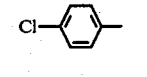— | 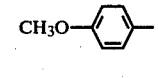— | VIS 040[2] | 0 | 3 |
| Na | CH₃—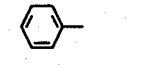— | Na | VIS 059[1] | 1 and 2, respect. in two experiments | 3[x] |
| Na | Cl—— | Na | VIS 066[1] | 2 and 0, respect. in two experiments | 3[x] |
| Na | CH₃O—⌬— | Na | VIS 067[1] | 1 in each of two experiments | 3[x] |
| Na | ⌬— | Na | VIS 041[2] | 0 | 3 |
| Na | Na | ⌬— | VIS 412[2] | 0 | 3 |
| ⌬— | Na | Na | VIS 422 | 1 | 3 (1,2) |

-continued

Test compound $$\begin{array}{c} R_1-O \\ \phantom{R}\diagdown \\ R_2-O \end{array} \overset{O}{\underset{}{\overset{\|}{P}}}-\overset{O}{\underset{}{\overset{\|}{C}}}-OR_3$$

| | | | | Score at day 5 | |
|---|---|---|---|---|---|
| $R_1$ | $R_2$ | $R_3$ | Code | treated | untreated |
| Na | Na | —⟨○⟩—C(=O)—O—C$_2$H$_5$ | VIS 242 | 1 | 2,5 (1,2) |
| Na | Na | —⟨○⟩—CH$_3$ | VIS 130 | 1 | 3 (1,2) |
| Na | Na | —⟨○⟩—O—CH$_3$ | VIS 239 | 1 | 3 (1,2) |
| Na | Na | —⟨○⟩—Cl | VIS 238 | 1 | 3 (1,2) |

[1] Treated in 0.1% Tween 80-10% aqueous glycerol
[x] In each of two experiments
[2] Start of treatment 24 hours after infection

III. Stability test

The acid stability was investigated by dissolving 5 mg of each compound in 1 ml of 0.1 N HCl in a test tube. For use as references 0.2 ml of each solution was withdrawn, immediately treated with 0.2 ml of a 10% aqueous solution of NaHCO$_3$ and frozen. The remaining 0.8 ml of each solution was incubated at 37° C. for 2 hours. After incubation, 0.8 ml of a 10% aqueous solution of NaHCO$_3$ was added to each solution and the solutions were frozen. The incubated compounds and the reference compounds were lyophilized to dryness and redissolved in distilled H$_2$O, 0.2 ml and 1.0 ml respectively, for each reference solution and incubated solution. The solutions were applied to silica gel (Merck PF$_{254}$, 20×20 cm) and polyethylene imine (Macherey-Nagel PEI, 20×20 cm) thin layer plates. A total of 20 μl of the reference solutions (100 μg compound) and 25 μl of the incubated solutions (100 μg compound) were applied. To each plate was also added, as references, solutions of phosphorous acid (H$_2$HPO$_3$) (5 and 20 μg) and of trisodiumphosphonoformate (5 and 20 μg). (Decomposition of phosphonoformic acid at low pH produces phosphorous acid).

The silica gel plates were prepared in duplicate and eluted with a solution composed of methanol-10% aq ammonia-trichloroacetic acid-water (50-15-5-3, v/v) and the polyethylene imine plates were eluted with a 1 M aq lithium chloride solution. After elution the plates were dried. One of the duplicated silica gel plates was sprayed with 4% aq (NH$_4$)$_2$MoO$_4$ and the polyethylene imine plates were sprayed with a solution composed of 60% HClO$_4$-0.1 N aq HCl-4% aq (NH$_4$)$_2$MoO$_4$-H$_2$O (5-10-25-60, v/v). The silica gel plates were briefly dried at 80°-90° C. and sprayed with 1% SnCl$_2$ in 10% aq HCl. Phosphorous acid and phosphonic acid groups appeared as blue spots on the silica gel plates (System 1) and as white spots on the polyethylene imine plates (System II). The remaining duplicate silica gel plates were exposed to iodine vapour for detection of di-and triesters of phosphonoformic acid.

| | $R_f$ System I | $R_f$ System II |
|---|---|---|
| Phosphorus acid | 0.31 | 0.71 |
| Na$_3$—phosphonoformate | 0 | 0.21 |

The formation of phosphorous acid and phosphonoformic acid in each incubated solution was estimated and the results are given below. The figures for the non-incubated reference compounds are given in parenthesis.

Test compound $$\begin{array}{c} R_1-O \\ \phantom{R}\diagdown \\ R_2-O \end{array} \overset{O}{\underset{}{\overset{\|}{P}}}-\overset{O}{\underset{}{\overset{\|}{C}}}-OR_3$$

| | | | | Estimated formation of | |
|---|---|---|---|---|---|
| | | | | | Na$_3$— |
| | | | | phosphorous | phosphono |
| $R_1$ | $R_2$ | $R_3$ | Code | acid (μg) | formate (μg) |
| Na | ⟨○⟩ | ⟨○⟩— | VIS 043 | N.D. (N.D.) | N.D. (N.D.) |
| Na | Na | Na | EHB 776 | 20 (N.D.) | (reference) |

N.D. = Not detectable (much less than 5 μg)

IV. In vivo metabolization

Metabolization of compounds of the invention was tested in NMRI 19–20 g male mice. The test compound (10 μmol) was dissolved in 0.5 ml saline and injected intraperitoneally. Two mice kept in one cage (for metabolization experiment) were used for each compound. The urine obtained from the two mice on day 1, 2 and 3 after the injections was collected. The urine was diluted with Tris-HCl buffer (pH 7.9) to a constant volume of 1 ml. This volume was then diluted 1:500, 1:5000 and 1:50000 with the same buffer and assayed for phosphonoformic acid activity on cell-free influenza polymerase. The assay mixture which includes Mn$^{2+}$ and assay conditions are described by Bishop, Obijeski and Simpson, J. Virol. 8, 66 (1971). Phosphonoformic acid in diluted urine gave 50% inhibition at 0.5 μM in this assay and was used as a standard to estimate the amount of phosphonoformic acid activity formed in the urine from compounds of the invention.

| Test compound | Recovered phosphonoformic acid activity in urine (μmol phosphonoformic acid) | | |
|---|---|---|---|
| | Day 1 | Day 2 | Day 3 |
| NaO—P(=O)(ONa)—C(=O)—O—C₆H₄—CH₃ VIS 130 | 1.25 | 0.25 | 0.10 |
| NaO—P(=O)(O—C₆H₅)—C(=O)—ONa VIS 041 | 1.00 | 0.25 | 0.25 |
| NaO—P(=O)(ONa)—C(=O)—ONa (reference) | 1.25 | 0.13 | <0.01 |

Acute toxicity

A preliminary acute toxicity test was carried out in mice. Groups of two male mice of the NMRI strain weighing 20-21 g received the test compound in doses of 62.5-500 mg/kg ip. The compound was given as a solution in 0.9% NaCl. The number of animals dead 24 hours after injection was as follows.

| Test compound | Dose mg/kg ip | No of animals dead / No of animals injected |
|---|---|---|
| VIS 412 | 62.5 | 0/2 |
| | 125 | 0/2 |
| | 250 | 0/2 |
| | 500 | 0/2 |
| VIS 043 | 62.5 | 0/2 |
| | 125 | 0/2 |
| | 250 | 0/2 |
| | 500 | 0/2 |
| VIS 041 | 62.5 | 0/2 |
| | 125 | 0/2 |
| | 250 | 0/2 |
| | 500 | 0/2 |

Discussion of test results

As seen in test I compounds of the invention are active on herpes virus and influenza virus multiplication in cells. As seen in test II compounds of the invention are also active on cutaneous herpes in the guinea pig. According to the stability test III, compounds of the invention are more stable than trisodium phosphonoformate in 0.1 M aqueous HCl, which is a model for stability in gastric juice, and the compounds of the invention should therefore be more suitable for oral administrations than phosphonoformic acid and physiologically acceptable salts thereof. The test on in vivo metabolism IV shows that compounds of the invention are metabolized to phosphonoformic acid measured as phosphonoformic acid activity on influenza polymerase. It is also shown in test IV that compounds according to the invention can give such an active metabolite in the urine of mice over a longer time period than trisodium phosphonoformate. Thus compounds of the invention have a prolonged activity in comparison with phosphonoformic acid and its physiologically acceptable salts. The acute toxicity test shows that compounds of the invention have a low acute toxicity, i.e. high LD50 values. In conclusion compounds of the invention have antiviral effects on herpes and influenza viruses and low toxicity. Furthermore compounds of the invention can be biotransformed to phosphonoformic acid or ionized forms thereof which have strong activities against viral functions and virus multiplication.

What is claimed is:

1. A compound of the formula $$R_1O-\underset{\underset{OR_2}{|}}{\overset{\overset{O}{\|}}{P}}-\overset{\overset{O}{\|}}{C}O-R_3 \quad \text{I}$$

wherein one of $R_1$ and $R_2$ is H and the other of $R_1$ and $R_2$ is a phenyl group of the formula

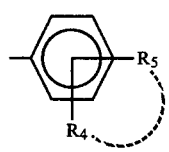

wherein $R_4$ and $R_5$ are the same or different and each is selected from the group consisting of hydrogen, halogen, alkyl having 1, 2, or 3 carbon atoms, alkoxy having 1, 2, or 3 carbon atoms, alkoxycarbonyl having 2-7 carbon atoms; and alkylcarbonyl groups having 2-7 carbon atoms; or $R_4$ and $R_5$ together form a straight saturated alkylene chain having 3 or 4 carbon atoms and being bound to adjacent positions, i.e. 2,3- or 3,4- in the phenyl ring and $R_3$ is H; and physiologically acceptable salts and optical isomers thereof.

2. A compound of the formula $$R_1O-\underset{\underset{OR_2}{|}}{\overset{\overset{O}{\|}}{P}}-\overset{\overset{O}{\|}}{C}O-R_3 \quad (I)$$

wherein one of $R_1$ and $R_2$ is H and the other of $R_1$ and $R_2$ is a phenyl group of the formula

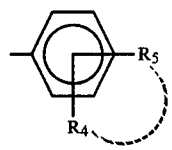

wherein $R_3$ is a phenyl group of formula II, wherein $R_4$ and $R_5$ are the same or different and each is selected from the group consisting of hydrogen, halogen, alkyl having 1, 2, or 3 carbon atoms, alkoxy having 1, 2, or 3 carbon atoms, alkoxycarbonyl having 2-7 carbon atoms; and alkylcarbonyl groups having 2-7 carbon atoms; or $R_4$ and $R_5$ together form a straight saturated alkylene chain having 3 or 4 carbon atoms and being bound to adjacent positions, i.e. 2,3— or 3,4— in the phenyl ring; and physiologically acceptable salts and optical isomers thereof.

3. A compound according to any of claims 1 or 2 wherein the radical II is a monosubstituted phenyl group.

4. A compound according to any of claims 1 or 2 wherein the radical II is a disubstituted phenyl group.

5. A compound according to any of claims 1 or 2 wherein $R_4$ and $R_5$ in the radical II together are trimethylene or tetramethylene.

6. A compound according to any of claims 1 or 2 wherein the radical II is an unsubstituted phenyl group.

7. A compound according to claim 1 wherein $R_1$ and $R_3$ are hydrogen and $R_2$ is a phenyl group of the Formula II, and sodium salts thereof.

8. A compound according to claim 2, wherein $R_1$ is hydrogen and $R_2$ and $R_3$ are phenyl.

9. A compound according to claim 2, wherein $R_1$ is hydrogen, $R_2$ is 4-methoxyphenyl and $R_3$ is phenyl.

10. A compound according to claim 2, wherein $R_1$ is hydrogen, $R_2$ is 4-chlorophenyl and $R_3$ is phenyl.

11. A compound according to claim 1, wherein $R_1$ and $R_3$ are hydrogen and $R_2$ is phenyl.

12. A compound according to claim 1, wherein $R_1$ and $R_3$ are hydrogen and $R_2$ is 4-methylphenyl.

13. A compound according to claim 1, wherein $R_1$ and $R_3$ are hydrogen and $R_2$ is 4-methoxyphenyl.

14. A compound according to claim 1, wherein $R_1$ and $R_3$ are hydrogen and $R_2$ is 4-chlorophenyl.

15. A compound according to claim 2, wherein $R_1$ is hydrogen, $R_2$ is 4-methylphenyl and $R_3$ is phenyl.

16. A compound according to claim 1, wherein $R_1$ and $R_3$ are hydrogen and $R_2$ is 2,6-dimethylphenyl.

17. A compound according to claim 1, wherein $R_1$ and $R_3$ are hydrogen and $R_2$ is 5-indanyl.

18. A compound according to claim 1, wherein $R_1$ and $R_3$ are hydrogen and $R_2$ is 4-acetylphenyl.

* * * * *